(12) United States Patent
Alberici et al.

(10) Patent No.: US 9,834,601 B2
(45) Date of Patent: Dec. 5, 2017

(54) ANTAGONISTS OF IL-17 ISOFORMS AND THEIR USES

(71) Applicant: Orega Biotech, Ecully (FR)

(72) Inventors: Gilles Alberici, Grezieu la Varenne (FR); Jeremy Bastid, Craponne (FR); Armand Bensussan, Paris (FR); Nathalie Bonnefoy, Lyons (FR); Jean-Francois Eliaou, Montpellier (FR)

(73) Assignee: Orega Biotech, Ecully (FR)

( * ) Notice: Subject to any disclaimer, the term of this patent is extended or adjusted under 35 U.S.C. 154(b) by 0 days.

(21) Appl. No.: 14/396,315

(22) PCT Filed: Jun. 11, 2013

(86) PCT No.: PCT/EP2013/062070
§ 371 (c)(1),
(2) Date: Oct. 22, 2014

(87) PCT Pub. No.: WO2013/186236
PCT Pub. Date: Dec. 19, 2013

(65) Prior Publication Data
US 2015/0104456 A1 Apr. 16, 2015

(30) Foreign Application Priority Data

Jun. 12, 2012 (WO) ................. PCT/EP2012/061134

(51) Int. Cl.
| | | |
|---|---|---|
| C07K 16/24 | (2006.01) | |
| A61K 39/395 | (2006.01) | |
| A61K 45/06 | (2006.01) | |
| A61K 39/00 | (2006.01) | |

(52) U.S. Cl.
CPC ........ *C07K 16/244* (2013.01); *A61K 39/3955* (2013.01); *A61K 45/06* (2013.01); *A61K 2039/505* (2013.01); *C07K 2317/76* (2013.01)

(58) Field of Classification Search
CPC ..... C07K 16/244; A61K 39/395; A61K 45/06
See application file for complete search history.

(56) References Cited

U.S. PATENT DOCUMENTS

| | | | |
|---|---|---|---|
| 4,683,195 A | 7/1987 | Mullis et al. | |
| 2007/0129302 A1* | 6/2007 | Gao et al. | 514/12 |
| 2009/0291097 A1* | 11/2009 | Chen | C07K 14/54 424/185.1 |

FOREIGN PATENT DOCUMENTS

| | | |
|---|---|---|
| WO | WO-2006094384 A1 | 9/2006 |
| WO | WO-2008049070 A2 | 4/2008 |
| WO | WO-2009136976 A2 | 11/2009 |
| WO | WO-2010116123 A1 | 10/2010 |
| WO | WO-2011044563 A2 | 4/2011 |
| WO | WO-2011141823 A2 | 11/2011 |

OTHER PUBLICATIONS

Furuta et al, Science translation Medicine, Apr. 2011; vol. 78, 78ra31, pp. 1-13.*
Bui et al; The Journal of Immunology, 2013, 190, 170.5.*
Phillips, A., J Pharm Pharmacology; 2001; 53: 1169-1174.*
Vidal et al. European Journal of Cancer.; 2005;41: 2812-2818.*
Pirollo et al. Cancer Res, 2008; 68(5): 1247-1250.*
<http://dtp.nci.nih.gov/branches/btb/ivclsp.html>, Attachment #1.*
<http://dtp.nci.nih.gov/branches/btb/hfa.html>,Attachment #2.*
Furuta eta l; www.sciencetranslationalmedicine.org/cgi/content/full/3/78/78ra31/DC1; 2011, Supplement).*
International Search Report and Written Opinion of the International Searching Authority for PCT/EP2013/062070 dated Sep. 5, 2013 (13 pages).
Yamaguchi, Yumi et al., "IL-17B and IL-17C Are Associated with TNF-α Production and Contribute to the Exacerbation of Inflammatory Arthritis," 2007 J Immunol, vol. 179, No. 10, pp. 7128-7136.
Goldstein, Robert H. et al., "Human Bone Marrow-Derived MSCs Can Home to Orthotopic Breast Cancer Tumors and Promote Bone Metastasis," 2010 Cancer Res., vol. 70, No. 24 pp. 10044-10050.
O'Sullivan, Timothy et al., "IL-17D Mediated Cancer Rejection," 2012 J Immunology, vol. 188, No. 162, p. 26.
Benatar, Tania et al., "IL-17E, a proinflammatory cytokine, has antitumor efficacy against several tumor types in vivo," 2010 Cancer Immunol Immunother, vol. 59, No. 6 pp. 805-817.
Iwakura, Yoichiro et al., "Functional Specialization of Interleukin-17 Family Members," 2011 Immunity, vol. 34, No. 2, pp. 149-162.
Gaffen, Sarah L. et al., "Structure and Signalling in the IL-17 Receptor Superfamily," 2009 Nat Rev Immunol., vol. 9, No. 8 (24 pages).
Gaffen, SL, "Structure and Signalling in the IL-17 Receptor Family," Erratum in 2009 Nat Rev Immunol., vol. 9, No. 10, p. 747.
Lee, J. et al., "IL-17E, a novel proinflammatory ligand for the IL-17 receptor homolog IL-17Rh1," 2001 J Biol Chem., vol. 276, No. 2 pp. 1660-1664.
Starnes, T et al., "Cutting edge: IL-17D, a novel member of the IL-17 family, stimulates cytokine production and inhibits hemopoiesis," 2002 J Immunol., vol. 169, No. 2, pp. 642-646.
Stamp, LK et al., "Different T cell subsets in the nodule and synovial membrane: absence of interleukin-17A in rheumatoid nodules," 2008 Arthritis Rheum, vol. 58, No. 6, pp. 1601-1608.
Wong, CK et al.,"Interleukin-25-induced chemokines and interleukin-6 release from eosinophils is mediated by p38 mitogen-activated protein kinase, c-Jun N-terminal kinase, and nuclear factor-kappaB," 2005 Am J Respir Cell Mol Biol., vol. 33, No. 2, pp. 186-194.
Ramirez-Carrozzi,V et al., "IL-17C regulates the innate immune function of epithelial cells in an autocrine manner," 2011 Nat Immunol., vol. 12, No. 12, pp. 1159-1166.

(Continued)

*Primary Examiner* — Bridget E Bunner
*Assistant Examiner* — Fozia Hamud
(74) *Attorney, Agent, or Firm* — Harris Beach PLLC

(57) ABSTRACT

The invention relates to antagonists of IL-17 isoforms and their uses in diagnosis and therapy, especially for the treatment or prevention of cancers or autoimmune and chronic inflammatory diseases.

6 Claims, 23 Drawing Sheets

(56) References Cited

OTHER PUBLICATIONS

Zhang, Jiang-Li et al., "Effect of interleukin-17D gene on the growth of xenografted tumor of human ovarian carcinoma in nude mice," 2014 Tumor, vol. 34, No. 8 (pp. 712-718) English Abstract on p. 712.

Stevceva, Liljana, "Cytokines and their antagonists as therapeutic agents," 2002 Curr Med Chem, 9(24), 2201-7, Abstract on p. 2201.

Hvid, Malene et al., "IL-25 in Atopic Dermatitis: A Possible Link between Inflammation and Skin Barrier Dysfunction?" 2011 Journal of Investigative Dermatology, vol. 131 (pp. 150-157).

Terashima, A., et al., "A novel subset of mouse NKT cells bearing the IL-17 receptor B responds to IL-25 and contributes to airway hyperreactivity", J Exp Med. Nov. 24, 2008; 205(12): 2727-2733.

Reppert, S., et al., "A role for T-bet-mediated tumour immune surveillance in anti-IL-17A treatment of lung cancer," Nat Commun. Dec. 20, 2011;2:600. doi: 10.1038/ncomms 1609.

Zhu, X, et al., "IL-17 expression by breast-cancer-associated macrophages: IL-17 promotes invasiveness of breast cancer cell lines," Breast Cancer Res. 2008;10(6):R95. doi: 10.1186/bcr2195.

R&D Systems, Mouse IL-17B Antibody, Catalog No. AF1709, Dec. 27, 2016, 1 page.

R&D Systems Human IL-17RB Antibody, Catalog No. MAB1207, Dec. 27, 2016, 1 page.

Haferlach T et al., J Clin Oncol. May 20, 2010;28(15):2529-37. doi: 10.1200/JCO.2009.23.4732.

Lavorgna A, Matsuoka M, Harhaj EW (2014) A Critical Role for IL-17RB Signaling in HTLV-1 Tax-Induced NF-?B Activation and T-Cell Transformation, PLoS Pathog 10(10): e1004418, 16pp. doi:10.1371/journal.ppat.1004418.

Liang Yet al., Proc Natl Acad Sci U S A. Apr. 19, 2005;102(16):5814-9.

Storz MN et al., J Invest Dermatol. May 2003;120(5):865-70.

Ren, L. et al. 2017. IL-17RB enhances thyroid cancer cell invasion and metastasis via ERK1/2 pathway-mediated MMP-9 expression. Molecular Immunology 90: 126-135.

* cited by examiner

IL-17 receptor E

IL-17D

```
                              SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Synthetic sequence, IL17B # NM_014443.2

<400> SEQUENCE: 1
gccactggac ctggtgtcac g                                                  21

<210> SEQ ID NO 2
<211> LENGTH: 22
<212> TYPE: DNA
<213> ORGANISM: Artificial Sequence
<220> FEATURE:
<223> OTHER INFORMATION: Synthetic sequence, IL17B # NM_014443.2

<400> SEQUENCE: 2
ctggggtcgt ggttgatgct gt                                                 22

<210> SEQ ID NO 3
<211> LENGTH: 20
<212> TYPE: DNA
<213> ORGANISM: Artificial Sequence
<220> FEATURE:
<223> OTHER INFORMATION: Synthetic sequence, IL17C # NM_013278.3

<400> SEQUENCE: 3
tgccaagtgg gggcaggctt                                                    20

<210> SEQ ID NO 4
<211> LENGTH: 24
<212> TYPE: DNA
<213> ORGANISM: Artificial Sequence
<220> FEATURE:
<223> OTHER INFORMATION: Synthetic sequence, IL17C # NM_013278.3

<400> SEQUENCE: 4
cgtgtccaca cggtatctcc aggg                                               24

<210> SEQ ID NO 5
<211> LENGTH: 23
<212> TYPE: DNA
<213> ORGANISM: Artificial Sequence
<220> FEATURE:
<223> OTHER INFORMATION: Synthetic sequence, IL17D # NM_138284.1

<400> SEQUENCE: 5
gccctgggcc tacagaatct cct                                                23

<210> SEQ ID NO 6
<211> LENGTH: 21
<212> TYPE: DNA
<213> ORGANISM: Artificial Sequence
<220> FEATURE:
<223> OTHER INFORMATION: Synthetic sequence, IL17D # NM_138284.1
```

```
<400> SEQUENCE: 6
cctcggtgta gacggaacgg c                                              21

<210> SEQ ID NO 7
<211> LENGTH: 20
<212> TYPE: DNA
<213> ORGANISM: Artificial Sequence
<220> FEATURE:
<223> OTHER INFORMATION: Synthetic sequence, IL17RB # NM_018725.3

<400> SEQUENCE: 7 tacccccgaga gccgaccgtt                                               20

<210> SEQ ID NO 8
<211> LENGTH: 21
<212> TYPE: DNA
<213> ORGANISM: Artificial Sequence
<220> FEATURE:
<223> OTHER INFORMATION: Synthetic sequence, IL17RB # NM_018725.3

<400> SEQUENCE: 8
ggcatctgcc cggagtaccc a                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic sequence, IL17RE # NM_153480.1

<400> SEQUENCE: 9
ccaccttcag gccatgcagc c                                              21

<210> SEQ ID NO 10
<211> LENGTH: 22
<212> TYPE: DNA
<213> ORGANISM: Artificial Sequence
<220> FEATURE:
<223> OTHER INFORMATION: Synthetic sequence, IL17RE # NM_153480.1

<400> SEQUENCE: 10
ctgtcatccg tgtgggaggc ca                                             22

<210> SEQ ID NO 11
<211> LENGTH: 20
<212> TYPE: DNA
<213> ORGANISM: Artificial Sequence
<220> FEATURE:
<223> OTHER INFORMATION: Synthetic sequence, GAPDH

<400> SEQUENCE: 11
gaaggtgaag gtcggagtca                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic sequence, GAPDH

<400> SEQUENCE: 12
gacaagcttc ccgttctcag                                                20

<210> SEQ ID NO 13
<211> LENGTH: 24
```

```
-continued

<212> TYPE: DNA
<213> ORGANISM: Artificial Sequence
<220> FEATURE:
<223> OTHER INFORMATION: Synthetic sequence, ACTIN

<400> SEQUENCE: 13
cagccatgta cgttgctatc cagg                                              24

<210> SEQ ID NO 14
<211> LENGTH: 23
<212> TYPE: DNA
<213> ORGANISM: Artificial Sequence
<220> FEATURE:
<223> OTHER INFORMATION: Synthetic sequence, ACTIN

<400> SEQUENCE: 14
aggtccagac gcaggatggc atg                                               23
```

ANTAGONISTS OF IL-17 ISOFORMS AND THEIR USES

CROSS-REFERENCE TO RELATED APPLICATIONS

This application is a national stage application under 35 U.S.C. §371 of PCT Application No. PCT/EP2013/062070, filed Jun. 11, 2013, which claims priority to and the benefit of PCT/EP2012/061134, filed Jun. 12, 2012, which is incorporated herein by reference in its entirety.

BACKGROUND OF THE INVENTION

Field of the Invention

The invention relates to antagonists of IL-17 isoforms and their uses in diagnosis and therapy, especially for the treatment or prevention of cancers or autoimmune and chronic inflammatory diseases.

Background

The interleukin 17 (IL-17) family comprises 6 interleukins (IL-17A, IL-17B, IL-17C, IL-17D, IL-17E=IL-25 and IL-17F) and their receptors (IL-17RA, IL-17RB, IL-17RC, IL-17RD and IL-17RE) (Gaffen, S. L. (2009) "Structure and signalling in the IL-17 receptor family" *Nature reviews. Immunology* 9(8): 556-567). IL-17A exists as a homodimer (IL-17A/A) or heterodimer (IL-17A/F) (Gaffen, S. L. (2009) "Structure and signalling in the IL-17 receptor family" *Nature reviews. Immunology* 9(8): 556-567).

IL-17A and IL-17F bind a trimeric complex of IL-17RA and IL-17RC whose expressions are ubiquitous. IL-17A and IL-17F are mainly produced by Th17 cells, a subset of T lymphocytes. The biological role of IL-17A and IL-17F is to participate to host defense against microbial or fungal infections by inducing an acute inflammatory response leading to release of pro-inflammatory cytokines, chemokines, antimicrobial peptides and matrix metalloproteinases from fibroblasts, keratinocytes, endothelial and epithelial cells (Iwakura, Y., H. Ishigame, et al. (2011) "Functional specialization of interleukin-17 family members" *Immunity* 34(2): 149-162). IL-17A also recruits neutrophils to the inflammatory sites (Iwakura, Y., H. Ishigame, et al. (2011) "Functional specialization of interleukin-17 family members" *Immunity* 34(2): 149-162). However, chronic or ectopic production of IL-17A and IL-17F is involved in the development of autoimmune and chronic inflammatory diseases as evidenced in mouse models of Experimental Autoimmune Encephalomyelitis, Collagen-Induced Arthritis (CIA) or SKG arthritic mice, in various models of colitis and psoriasis (Iwakura, Y., H. Ishigame, et al. (2011) "Functional specialization of interleukin-17 family members" *Immunity* 34(2): 149-162). In humans, IL-17A and/or IL-17F are for instance involved in Rheumatoid Arthritis (RA), Multiple Sclerosis, Systemic Lupus Erythematosus inflammatory bowel diseases, Crohn's diseases and psioriasis (Iwakura, Y., H. Ishigame, et al. (2011) "Functional specialization of interleukin-17 family members" *Immunity* 34(2): 149-162). IL-17A triggers a positive feedback loop on IL-6 signaling, including activation of the NFκB and Stat3 in fibroblasts, leading to chronic inflammation. IL-17A and IL-17F are also involved in allergic diseases (Iwakura, Y., H. Ishigame, et al. (2011) "Functional specialization of interleukin-17 family members" *Immunity* 34(2): 149-162).

The 4 other members of the family were identified recently based on sequence homology, but have been poorly studied so far. IL-17B binds IL-17RB; IL-17C binds IL-17RE, IL-17E binds a complex of IL-17RA and IL-17RB; the receptor of IL-17D is unknown (Gaffen, S. L. (2009) "Structure and signalling in the IL-17 receptor family" *Nature reviews. Immunology* 9(8): 556-567). IL-17B, IL-17C, IL-17D and IL-17E activate pathways and cytokines release similar to those induced by IL-17A and IL-17F such as NFκb, TNFα, IL-6, IL-8, IL-1β (Lee, J., W. H. Ho, et al. (2001) "IL-17E, a novel proinflammatory ligand for the IL-17 receptor homolog IL-17Rh1" *J Biol Chem* 276(2): 1660-1664; Starnes, T., H. E. Broxmeyer, et al. (2002) "Cutting edge: IL-17D, a novel member of the IL-17 family, stimulates cytokine production and inhibits hemopoiesis" *J Immunol* 169(2): 642-646; Stamp, L. K., A. Easson, et al. (2008) "Different T cell subsets in the nodule and synovial membrane: absence of interleukin-17A in rheumatoid nodules" *Arthritis Rheum* 58(6): 1601-1608; Iwakura, Y., H. Ishigame, et al. (2011) "Functional specialization of interleukin-17 family members" *Immunity* 34(2): 149-162; Ramirez-Carrozzi, V., A. Sambandam, et al. (2011) "IL-17C regulates the innate immune function of epithelial cells in an autocrine manner" *Nat Immunol* 12(12): 1159-1166). As IL-17A and IL-17F, IL-17C is important for the defense against bacterial infections (Ramirez-Carrozzi, V., A. Sambandam, et al. (2011) "IL-17C regulates the innate immune function of epithelial cells in an autocrine manner" *Nat Immunol* 12(12): 1159-1166). As IL-17A and IL-17F, IL-17B and IL-17C also play a role in CIA in mice (Yamaguchi (2007) "IL-17B and IL-17C are associated with TNF-α production and contribute to the exacerbation of inflammatory arthritis" *J. Immunol* 179: 7128-7136) and expression of IL-17A, IL-17B, IL-17D, IL-17E have been detected in human RA nodules (Stamp, L. K., A. Easson, et al. (2008) "Different T cell subsets in the nodule and synovial membrane: absence of interleukin-17A in rheumatoid nodules" *Arthritis Rheum* 58(6): 1601-1608). IL-17E, originally named IL-25, is the most divergent member of the family. It has some common (NFκB, IL-6, IL-8) and unique (IL-4, IL-5, and IL-13) targets (Wong, C. K., P. F. Cheung, et al. (2005) "Interleukin-25-induced chemokines and interleukin-6 release from eosinophils is mediated by p38 mitogen-activated protein kinase, c-Jun N-terminal kinase, and nuclear factor-kappaB" *American journal of respiratory cell and molecular biology* 33(2): 186-194; Iwakura, Y., H. Ishigame, et al. (2011) "Functional specialization of interleukin-17 family members" *Immunity* 34(2): 149-162). IL-17E is involved in asthma by inducing Th2 cell cytokines (Iwakura, Y., H. Ishigame, et al. (2011) "Functional specialization of interleukin-17 family members" *Immunity* 34(2): 149-162).

In conclusion, it seems that all isoforms exhibit some redundancy of biological functions and targets (although they are produced by different cell types) and may have similar capacity to induce inflammatory mediators such as IL-6 or TNFα and activate oncogenic pathways such as NFκB and Stat3.

Increased IL-17A or IL-17A producing cells (e.g, Th17 cells) have been reported in numerous solid and hematological cancers and may thus be therapeutic target in cancers (Iwakura, Y., H. Ishigame, et al. (2011) "Functional specialization of interleukin-17 family members" *Immunity* 34(2): 149-162). In contrast, the expression and role of IL-17B, IL-17C, IL-17D, IL-17E and IL-17F have not been evaluated in cancers.

DETAILED DESCRIPTION OF THE INVENTION

Definitions

Unless otherwise expressly defined, the terms used herein are to be understood according to their ordinary meaning in the art. Terms used in the singular or referred to as "a" or "an" also include the plural and vice versa, unless otherwise specified or indicated by context. Standard techniques and procedures are generally performed according to conventional methods in the art and various general references (see generally, Sambrook et al. Molecular Cloning: A Laboratory Manual, 2nd ed. (1989) Cold Spring Harbor Laboratory Press, Cold Spring Harbor, N.Y.), which are provided throughout this document.

As used herein, the term "IL-17" denotes the IL-17 protein or interleukin 17, advantageously of human origin.

As used herein, the term "IL-17 isoform" refers to IL-17A, IL-17B, IL-17C, IL-17D, IL-17E=IL-25 or IL-17F.

As used herein, the term "IL-17 antagonist" refers to an agent, substance, molecule, etc., that disrupts, prevents, inhibits, or otherwise targets and/or interferes with the activity of IL-17 or the IL-17 pathway. Non-limiting examples of IL-17 antagonists include antibodies against IL-17 or its receptor (including, for example, neutralizing antibodies), small molecule antagonists, decoy receptors, protein antagonists (including fusion proteins and glycoproteins), and nucleic acid antagonists (e.g., gene silencers, short hairpin RNA, or "shRNA", siRNA, and antisense nucleic acid molecules).

As used herein, the term "antibody" (or "immunoglobulin") includes whole or "full" antibodies and any antigen binding fragment or single chains thereof. An "antibody" refers to a glycoprotein comprising at least two heavy (H) chains and two light (L) chains inter-connected by disulfide bonds, or an antigen binding portion thereof. A full heavy chain contains a heavy chain variable region ($V_H$) and a heavy chain constant region. A full heavy chain constant region has three domains, $C_H1$, $C_H2$ and $C_H3$. A full light chain contains a light chain variable region ($V_L$) and a light chain constant region that contains one domain, $C_L$. The $V_H$ and $V_L$ regions can be further subdivided into regions of hypervariability, termed complementarity determining regions (CDR), situated within the more conserved framework regions (FR). Each full $V_H$ and $V_L$ contains three CDRs and four FRs, arranged from amino-terminus to carboxy-terminus in the following order: FR1, CDR1, FR2, CDR2, FR3, CDR3, FR4. The $V_H$ and $V_L$ form a binding domain that interacts with an antigen. The constant regions of the antibodies may mediate the binding of the immunoglobulin to host tissues or factors, including various cells of the immune system (e.g., effector cells) and the first component (Clq) of the classical complement system.

As used herein, the term "antigen-binding fragment" refers to one or more fragments of an antibody that retain the ability to specifically bind to an antigen (e.g., IL-17). The antigen-binding function of an antibody can be performed by fragments of a full antibody. Examples of "antigen-binding fragments" include (i) an Fab fragment, a monovalent fragment consisting of the $V_L$, $V_H$, $C_L$ and $C_H1$ domains; (ii) an F(ab)$_2$ fragment, a bivalent fragment comprising two Fab fragments linked by a disulfide bridge at the hinge region; (iii) an Fab' fragment, an Fab with part of the hinge region (see, FUNDAMENTAL IMMUNOLOGY, Paul ed., 3$^{rd}$ ed. 1993); (iv) an Fd fragment, consisting of the $V_H$ and $C_H1$ domains; (v) an Fv fragment consisting of the $V_L$ and $V_H$ domains of a single arm of an antibody, (vi) a dAb fragment (Ward et al., (1989) Nature 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "diabodies" refers to small antibody fragments with two antigen binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites.

By "purified" and "isolated" it is meant, when referring to a polypeptide (e.g. an antibody) or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

As used herein, the term "monoclonal antibody" refers to a preparation of antibody molecules of single molecular composition. A monoclonal antibody composition displays a single binding specificity and affinity for a particular epitope of an antigen (i.e., IL-17).

As used herein, the term "human antibody" is intended to include antibodies having variable regions in which both the framework and CDR regions are derived from human germline immunoglobulin sequences. If the antibody contains a constant region, the constant region also is derived from human germline immunoglobulin sequences. Human antibodies for use in the invention may include amino acid residues not encoded by human germline immunoglobulin sequences (e.g., mutations introduced by random or site-specific mutagenesis in vitro or by somatic mutation in vivo).

As used herein, the term "humanized antibody" refers to antibodies in which CDR sequences derived from the germline of another mammalian species, such as a mouse, rat, or rabbit, have been grafted onto human framework sequences. Additional framework region modifications may be made within the human framework sequences.

As used herein, the term "chimeric antibody" refers to antibodies in which the variable region sequences are derived from one species and the constant region sequences are derived from another species, such as an antibody in which the variable region sequences are derived from a mouse, rat, or rabbit antibody and the constant region sequences are derived from a human antibody.

As used herein, the term "small molecule" includes, but is not limited to organic or inorganic compounds (including heterorganic and organometallic compounds) having a molecular weight of less than 1000 grams per mole, more specifically less than 750 grams per mole, and even more specifically, 500 grams per mole. Salts, esters, and other pharmaceutically acceptable forms of such compounds are also encompassed.

As used herein, the term "nucleic acid antagonist" is intended to include any gene silencing molecule or tool such as shRNA ("short hairpin RNA" or "small hairpin RNA") or interfering RNA ("RNAi" or small interfering RNA, "siRNA").

As used herein, the term "subject" or "patient" refers to a mammalian animal (including but not limited to non-primates such as cows, pigs, horses, sheep, cows, dogs, cats, rats, and mice), more specifically a primate (including but not limited to monkeys, apes, and humans), and even more specifically, a human.

In the context of the invention, the term "treating" or "treatment", as used herein, means reversing, alleviating, inhibiting the progress of, or preventing the disorder or condition to which such term applies, or one or more symptoms of such disorder or condition. A "therapeutically effective amount" is intended for a minimal amount of active agent which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder. The amount of a therapeutic agent that is effective to alleviate any particular disease symptom or effect (also referred to as the "therapeutically effective amount") or prevent a particular disease symptom or effect (also referred to as the "prophylactically effective amount") may vary according to factors such as the disease state, age, and weight of the patient, and the ability of the drug to elicit a desired response in the patient. Whether a disease symptom or effect has been alleviated can be assessed by any clinical measurement typically used (e.g., by healthcare providers or laboratory clinicians) to assess the severity or progression status of that symptom or effect.

As used herein, the term "prevent" or "prevention" or "prophylactic" or "prophylaxis" refers to the inhibition of the development, onset, or recurrence of a symptom, effect, disease, or disorder (e.g., a cell proliferation disorder) in a subject which has not yet been diagnosed as having it.

As used herein, the term "reference amount" or "reference level" refers to an established amount or expression level of a substance or molecule, e.g., a protein, nucleic acid, enzyme, etc., to which an amount of the same substance or molecule measured from a subject sample is being compared. For example, a reference amount may be an amount of a protein found in a normal tissue sample (or an average amount from a population of tissue samples) to which the amount of a protein from a diseased (e.g., cancerous) tissue sample is compared.

As used herein, the term "expression" or "expressed" refers to the transcription of RNA (e.g., mRNA) from a nucleic acid template. "Expression" or "expressed" may also refer to translation of mRNA into a polypeptide. The term "expression" or "expressed" is also intended to include the production of a gene product or polypeptide that is released and/or secreted by a cell. In some instances, the term "produced" or "production" is used to indicate the expression of a gene product or polypeptide that is secreted or released by a cell (e.g., into the extracellular environment or, if the cell is in vitro, into the culture medium). The term "increased expression" is intended to include an alteration in gene expression at least at the level of increased mRNA production and/or at the level of polypeptide expression, generally resulting in an increased amount of a gene product or protein. In some instances, "increased expression" is used interchangeably with the term "overexpression" or "over-expressed".

As used herein, the term "likely to respond" means that a subject is more likely than not to receive a therapeutic benefit from the therapeutic agent, e.g., that the therapeutic agent is more likely than not to achieve the desired effect, such as, to alleviate one or more disease symptoms or effects. In one specific example, a subject who has a cell proliferation disorder in which levels of an IL-17 isoform are increased compared to a reference amount of each factor is more likely to respond to treatment of the cell proliferation disorder with an antagonist of said IL-17 isoform.

As used herein, the term "sample" refers any biological fluid, cell, tissue, or other component from a subject. Samples include, without limitation, tissue fragments (diseased or non-diseased), organs, cells, cellular components, whole blood, serum, plasma, saliva, urine, synovial fluid, bone marrow, cerebrospinal fluid, vaginal mucus, cervical mucus, nasal secretions, sputum, semen, amniotic fluid, bronchoalveolar lavage fluid, cellular exudates, and tumor fragments.

Description of the Invention

The inventors have found that all IL-17 isoforms are upregulated in human cancers or cancer cell lines, or secreted by immune cells that infiltrate the tumors. Moreover, all IL-17 isoforms display similar oncogenic properties: they stimulate cancer cell proliferation, increase cancer cell invasion and may induce the secretion of pro-inflammatory mediators such as IL-6. Thus, all IL-17 isoforms may be therapeutic targets for cancer.

According to a first aspect, the invention provides a method of identifying a subject with cancer or an increased likelihood of developing a cancer, said method comprising measuring the amount of at least one IL-17 isoform selected from the group consisting of IL-17B, IL-17C, IL17D, IL-17E and possibly IL-17F in a sample of said subject, wherein an increased expression or production of at least one IL-17 isoform selected from the group consisting of IL-17B, IL-17C, IL17D, IL-17E and possibly IL-17F indicates that the subject has a cancer or has an increased likelihood of developing a cancer.

According to another aspect, the present invention relates to a composition comprising at least one IL-17 antagonist of at least one IL-17 isoform selected from the group consisting of IL-17B, IL-17C, IL17D, IL-17E and IL-17F for its use for the treatment or prevention of cell proliferation disorders or cancers.

According to another aspect, the present invention relates to a composition comprising at least one IL-17 antagonist of at least one IL-17 isoform selected from the group consisting of IL-17B, IL-17C, IL17D, IL-17E and IL-17F for its use for the treatment or prevention of a cell proliferation disorder or a cancer in a subject having an increased amount (expression or production) of said IL-17 isoform.

The invention provides a method of treating a cell proliferation disorder, advantageously a cancer, in a subject, said method comprising administering to said subject a composition comprising at least one IL-17 antagonist of at least one IL-17 isoform selected from the group consisting of IL-17B, IL-17C, IL17D, IL-17E and IL-17F, in an amount effective to treat said cell proliferation disorder or cancer.

The invention also provides a method of preventing a cell proliferation disorder, advantageously a cancer, in a subject at increased risk for a cell proliferation or cancer, said method comprising administering to said subject a composition comprising at least one IL-17 antagonist of at least one IL-17 isoform selected from the group consisting of IL-17B, IL-17C, IL17D, IL-17E and IL-17F, in an amount effective to prevent said cell proliferation disorder or cancer.

In one aspect, the method of the invention further comprises measuring the amount of at least one IL-17 isoform selected from the group consisting of IL-17B, IL-17C, IL17D, IL-17E and IL-17F in a sample from said subject, and comparing the measured amount to a reference amount to determine if said subject is likely to respond to the administration of said composition, wherein an amount (expression or production) of said IL-17 isoform greater than said reference amount indicates that the subject is likely to respond.

In some embodiments of the invention, the sample is selected from the group consisting of an organ sample, a tissue sample, a cell sample and a blood sample. In some embodiments, the sample comprises cancer cells.

In a particular embodiment, the composition comprises at least one IL-17 antagonist of at least one IL-17 isoform selected from the group consisting of IL-17B, IL-17C, IL17D, and IL-17E. In other words, the composition comprises at least an antagonist of IL-17B or at least an antagonist of IL-17C or at least an antagonist of IL-17D or at least an antagonist of IL-17E.

In another particular embodiment, the composition comprises at least one IL-17 antagonist of at least one IL-17 isoform selected from the group consisting of IL-17B, IL-17C and IL-17D. In other words, the composition comprises at least an antagonist of IL-17B or at least an antagonist of IL-17C or at least an antagonist of IL-17D.

Examples of cell proliferation disorders or cancers include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

Typically, the composition of the present invention is useful for the prevention or treatment of breast cancer, colon cancer, gastric cancer, glioma, hepatocellular carcinoma, kidney cancer, leukemia, lung cancer, lymphoma, melanoma, multiple myeloma, ovarian cancer, pancreatic cancer, prostate cancer.

Advantageously, the treatment is for:
targeting and/or killing the cancer cells or the cells at increased risk for becoming cancerous;
increasing the effectiveness of a therapeutic agent, advantageously a chemotherapeutic agent; and/or
preventing tumor metastasis.

The invention provides a method of targeting and/or killing the cancer cells or the cells at increased risk for becoming cancerous in a subject, said method comprising administering to said subject a composition comprising at least one IL-17 antagonist of at least one IL-17 isoform selected from the group consisting of IL-17B, IL-17C and IL17D, and possibly IL-17E and IL-17F, in an amount effective to target and/or kill the cancer cells or the cells at increased risk for becoming cancerous.

The invention provides a method of increasing the effectiveness of a therapeutic agent for killing abnormally proliferating cells in a subject having a cell proliferation disorder or cancer, said method comprising administering an amount of a composition comprising at least one IL-17 antagonist of at least one IL-17 isoform selected from the group consisting of IL-17B, IL-17C and IL17D, and possibly IL-17E and IL-17F, effective to increase the effectiveness of said therapeutic agent at a time selected from the group consisting of before, during or after administration of said therapeutic agent.

Advantageously, said therapeutic agent is a chemotherapeutic agent. More preferably said chemotherapeutic agent is selected from the group consisting of: doxorubicin, paclitaxel, tamoxifen, cisplatin, vincristine, and vinblastine.

The invention also provides a method of preventing tumor metastases in a subject having a cell proliferation disorder or cancer, said method comprising administering an amount of a composition comprising at least one IL-17 antagonist of at least one IL-17 isoform selected from the group consisting of IL-17B, IL-17C and IL17D, and possibly IL-17E and IL-17F, effective to prevent tumor metastases in said subject.

Alternatively, a composition as disclosed above (comprising at least one IL-17 antagonist of at least one IL-17 isoform selected from the group consisting of IL-17B, IL-17C, IL17D, IL-17E and IL-17F, advantageously comprising at least one IL-17 antagonist of at least one IL-17 isoform selected from the group consisting of IL-17B, IL-17C, IL17D and IL-17E, more advantageously comprising at least one IL-17 antagonist of at least one IL-17 isoform selected from the group consisting of IL-17B, IL-17C and IL-17D) can be used for the treatment or prevention of autoimmune and chronic inflammatory diseases, for example Rheumatoid Arthritis, Multiple Sclerosis, Systemic Lupus Erythematosus, inflammatory bowel diseases, Crohn's diseases, psoriasis, ulcerative colitis or atopic dermatitis.

In a particular embodiment, the composition further comprises one IL-17 antagonist of any IL-17 isoform, preferably of another Il-17 isoform. According to the invention, the expression "of another IL-17 isoform" means that, if the first antagonist is an antagonist of a first IL-17 isoform, then if the composition comprises at least another antagonist (a second antagonist), this second antagonist is an antagonist of a second (different) IL-17 isoform.

More specifically, if the first antagonist is an antagonist of IL-17B, then an antagonist of another Il-17 isoform is preferably an antagonist of IL-17A, IL-17C, IL-17D, IL-17E or IL-17F. According to a particular embodiment, if the first antagonist is an antagonist of IL-17B, then the antagonist of another Il-17 isoform is preferably not an antagonist of IL-17E.

More specifically, if the first antagonist is an antagonist of IL-17C, then an antagonist of another Il-17 isoform is preferably an antagonist of IL-17A, IL-17B, IL-17D, IL-17E or IL-17F.

More specifically, if the first antagonist is an antagonist of IL-17D, then an antagonist of another Il-17 isoform is preferably an antagonist of IL-17A, IL-17B, IL-17C, IL-17E or IL-17F.

According to this embodiment and as an example, the composition may comprise:

an antagonist of IL-17B and an antagonist of IL-17A; or
an antagonist of IL-17B and an antagonist of IL-17C; or
an antagonist of IL-17B and an antagonist of IL-17D; or
an antagonist of IL-17B and an antagonist of IL-17E; or
an antagonist of IL-17B and an antagonist of IL-17F; or possibly
an antagonist of IL-17B and another antagonist of IL-17B; or
an antagonist of IL-17C and an antagonist of IL-17A; or
an antagonist of IL-17C and an antagonist of IL-17D; or
an antagonist of IL-17C and an antagonist of IL-17E; or
an antagonist of IL-17C and an antagonist of IL-17F; or possibly
an antagonist of IL-17C and another antagonist of IL-17C; or
an antagonist of IL-17D and an antagonist of IL-17A; or
an antagonist of IL-17D and an antagonist of IL-17E; or
an antagonist of IL-17D and an antagonist of IL-17F; or possibly
an antagonist of IL-17D and another antagonist of IL-17D;
or possibly
an antagonist of IL-17E and an antagonist of IL-17A; or
an antagonist of IL-17E and an antagonist of IL-17F; or possibly
an antagonist of IL-17E and another antagonist of IL-17E; or possibly
an antagonist of IL-17F and another antagonist of IL-17F.

Alternatively, the composition comprises one IL-17 antagonist of one IL-17 isoform selected from the group consisting of IL-17B, IL-17C and IL17D, and possibly IL-17E and IL-17F, wherein said antagonist is also an antagonist of at least another IL-17 isoform. According to the invention, the expression "of another IL-17 isoform" means that if the first antagonist is an antagonist of a first IL-17 isoform, then it is also an antagonist of a second (different) IL-17 isoform.

More specifically, if the antagonist is an antagonist of IL-17B, then it is also preferably an antagonist of IL-17A, IL-17C, IL-17D, IL-17E or IL-17F. According to a particular embodiment, if the antagonist is an antagonist of IL-17B, then it is preferably not an antagonist of IL-17E.

More specifically, if the antagonist is an antagonist of IL-17C, then it is also preferably an antagonist of IL-17A, IL-17B, IL-17D, IL-17E or IL-17F.

More specifically, if the antagonist is an antagonist of IL-17D, then it is also preferably an antagonist of IL-17A, IL-17B, IL-17C, IL-17E or IL-17F.

According to this embodiment and as an example, the composition may comprise:

an antagonist of IL-17B, which is also an antagonist of IL-17A; or
an antagonist of IL-17B, which is also an antagonist of IL-17C; or
an antagonist of IL-17B, which is also an antagonist of IL-17D; or
an antagonist of IL-17B, which is also an antagonist of IL-17E; or
an antagonist of IL-17B, which is also an antagonist of IL-17F; or
an antagonist of IL-17C, which is also an antagonist of IL-17A; or
an antagonist of IL-17C, which is also an antagonist of IL-17D; or
an antagonist of IL-17C, which is also an antagonist of IL-17E; or an antagonist of IL-17C, which is also an antagonist of IL-17F; or an antagonist of IL-17D, which is also an antagonist of IL-17A; or an antagonist of IL-17D, which is also an antagonist of IL-17E; or an antagonist of IL-17D, which is also an antagonist of IL-17F;

or possibly an antagonist of IL-17E, which is also an antagonist of IL-17A; or an antagonist of IL-17E, which is also an antagonist of IL-17F.

In a particular embodiment, the antagonist is an antibody that binds to at least 2 isoforms of IL-17. An antibody which binds to both IL-17A and IL-17F and only to these specific 2 isoforms is advantageously excluded. In other words, an antibody according to the invention can bind to at least:

IL-17A and IL-17B; or
IL-17A and IL-17C; or
IL-17A and IL-17D; or
IL-17A and IL-17E; or
IL-17B and IL-17C; or
IL-17B and IL-17D; or
IL-17B and IL-17E; or
IL-17B and IL-17F; or
IL-17C and IL-17D; or
IL-17C and IL-17E; or
IL-17C and IL-17F; or
IL-17D and IL-17E; or
IL-17D and IL-17F; or
IL-17E and IL-17F.

In another embodiment, the composition further comprises two (2) IL-17 antagonists of any IL-17 isoform, preferably of other IL-17 isoforms.

Alternatively, the composition comprises one IL-17 antagonist of one IL-17 isoform selected from the group consisting of IL-17B, IL-17C and IL17D, and possibly IL-17E and IL-17F, wherein said antagonist is also an antagonist of at least two (2) other IL-17 isoforms.

In another embodiment, the composition further comprises three (3) IL-17 antagonists of any IL-17 isoform, preferably of other Il-17 isoforms.

Alternatively, the composition comprises one IL-17 antagonist of one IL-17 isoform selected from the group consisting of IL-17B, IL-17C and IL17D, and possibly IL-17E and/or IL-17F, wherein said antagonist is also an antagonist of at least three (3) other IL-17 isoforms.

In another embodiment, the composition further comprises four (4) IL-17 antagonists of any IL-17 isoform, preferably of other Il-17 isoforms.

Alternatively, the composition comprises one IL-17 antagonist of one IL-17 isoform selected from the group consisting of IL-17B, IL-17C and IL17D, and possibly IL-17E and/or IL-17F wherein said antagonist is also an antagonist of at least four (4) other IL-17 isoforms.

In another embodiment, the composition comprises IL-17 antagonists of all IL-17 isoforms, i.e.:

an antagonist of IL-17A; and
an antagonist of IL-17B; and
an antagonist of IL-17C; and
an antagonist of IL-17D; and
an antagonist of IL-17E; and
an antagonist of IL-17F.

Alternatively, the composition comprises an IL-17 antagonist which is an antagonist of all the IL-17 isoforms (IL-17A, IL-17B, IL-17C, IL-17D, IL-17E and IL-17F).

In a particular embodiment, the antagonist is an antibody which binds to and possibly neutralizes all the isoforms of IL-17 (to IL-17A, IL-17B, IL17-C, IL-17D, IL-17E and IL-17F), i.e. a multi-isoform IL-17 antibody.

In one embodiment, the antagonist is an antibody or an antigen binding antibody fragment.

In one embodiment, said antibody is a humanized or human antibody.

In one embodiment, said antibody is a monoclonal antibody.

More generally, the present invention also concerns a novel composition which comprises:

at least one IL-17 antagonist of at least one IL-17 isoform selected from the group consisting of Il-17B, IL-17C, IL-17D and IL-17E and one IL-17 antagonist of another Il-17 isoform; or at least one IL-17 antagonist of at least one IL-17 isoform selected from the group consisting of IL-17B, IL-17C, IL17-D and IL-17E, said antagonist being also an antagonist of at least another IL-17 isoform.

The expression "of another Il-17 isoform" is as defined above.

According to a particular embodiment, the present invention concerns a novel composition which comprises:

at least one IL-17 antagonist of at least one IL-17 isoform selected from the group consisting of Il-17B, IL-17C and IL-17D and one IL-17 antagonist of another Il-17 isoform; or at least one IL-17 antagonist of at least one IL-17 isoform selected from the group consisting of IL-17B, IL-17C and IL17D, said antagonist being also an antagonist of at least another IL-17 isoform.

To advantage, the composition does not comprise:

the specific combination of an antagonist of IL-17A and an antagonist of IL-17F; or one antagonist of IL-17A which is also an antagonist of IL-17F; or the specific combination of an antagonist of IL-17B and an antagonist of IL-17E; or one antagonist of IL-17B which is also an antagonist of IL-17E.

In one embodiment, the composition comprises IL-17 antagonists of all IL-17 isoforms, i.e.:

an antagonist of IL-17A; and
an antagonist of IL-17B; and
an antagonist of IL-17C; and
an antagonist of IL-17D; and
an antagonist of IL-17E; and
an antagonist of IL-17F.

Alternatively, the composition comprises one IL-17 antagonist which is an antagonist of all the IL-17 isoforms (IL-17A, IL-17B, IL-17C, IL-17D, IL-17E and IL-17F).

In a particular embodiment, the antagonist is an antibody which binds to and possibly neutralizes all the isoforms of IL-17 (to IL-17A, IL-17B, IL17-C, IL-17D, IL-17E and IL-17F), i.e. a multi-isoform IL-17 antibody.

In one embodiment, the antagonist is an antibody or an antigen binding antibody fragment.

In one embodiment, said antibody is a humanized or human antibody.

In one embodiment, said antibody is a monoclonal antibody.

The composition of the invention has a general interest in diagnosis and therapy.

In one embodiment and as previously mentioned, said composition is useful for the treatment or prevention of cell proliferation disorders or cancers.

Typically, the composition of the present invention is useful for the prevention or treatment of breast cancer, colon cancer, gastric cancer, glioma, hepatocellular carcinoma, kidney cancer, leukemia, lung cancer, lymphoma, melanoma, multiple myeloma, ovarian cancer, pancreatic cancer, prostate cancer.

Advantageously, the treatment is for:
targeting and/or killing the cancer cells or the cells at increased risk for becoming cancerous;
increasing the effectiveness of a therapeutic agent, advantageously a chemotherapeutic agent; and/or
preventing tumor metastasis.

In one embodiment, said composition is useful for the treatment or prevention of autoimmune and chronic inflammatory diseases.

Immune-related and inflammatory diseases include for example: systemic lupus erythematosus, arthritis, psoriatic arthritis, rheumatoid arthritis, osteoarthritis, juvenile chronic arthritis, spondyloarthropathies, systemic sclerosis, idiopathic inflammatory myopathies, Sjogren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems such as multiple sclerosis, idiopathic demyelinating polyneuropathy or Guillain-Barre syndrome, amyotrophic lateral sclerosis and chronic inflammatory demyelinating polyneuropathy, hepatobiliary diseases such as infectious, autoimmune chronic active hepatitis, primary biliary cirrhosis, granulomatous hepatitis, sclerosing cholangitis, inflammatory bowel disease, colitis, Crohn's disease gluten-sensitive enteropathy, and endotoxemia, autoimmune or immune-mediated skin diseases including bullous skin diseases, erythema multiforme and atopic and contact dermatitis, psoriasis, neutrophilic dermatoses, cystic fibrosis, allergic diseases such as asthma, allergic rhinitis, food hypersensitivity and urticaria, cystic fibrosis, immunologic diseases of the lung such as eosinophilic pneumonia, idiopathic pulmonary fibrosis, adult respiratory disease (ARD), acute respiratory distress syndrome (ARDS) and inflammatory lung injury such as asthma, chronic obstructive pulmonary disease (COPD), airway hyper-responsiveness, chronic bronchitis, allergic asthma and hypersensitivity pneumonitis, transplantation associated diseases including graft and organ rejection and graft-versus-host-disease, septic shock, multiple organ failure, obesity, type 2 diabetes, non alcoholic liver cirrhosis, non alcoholic liver disease, oncology (tumor angiogenesis, primary tumors and metastases).

Among the autoimmune and chronic inflammatory disease, preferred diseases are: Rheumatoid Arthritis, Multiple Sclerosis, Systemic Lupus Erythematosus, inflammatory bowel diseases, Crohn's diseases, psoriasis, ulcerative colitis, atopic dermatitis.

Diagnostic and Therapeutic Applications of the Compositions of the Invention
Therapeutics Advantageously, an IL-17-mediated disease is immune-related and inflammatory diseases, including for example, systemic lupus erythematosus, arthritis, psoriatic arthritis, rheumatoid arthritis, osteoarthritis, juvenile chronic arthritis, spondyloarthropathies, systemic sclerosis, idiopathic inflammatory myopathies, Sjogren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems such as multiple sclerosis, idiopathic demyelinating polyneuropathy or Guillain-Barre syndrome, amyotrophic lateral sclerosis and chronic inflammatory demyelinating polyneuropathy, hepatobiliary diseases such as infectious, autoimmune chronic active hepatitis, primary biliary cirrhosis, granulomatous hepatitis, sclerosing cholangitis, inflammatory bowel disease, colitis, Crohn's disease gluten-sensitive enteropathy, and endotoxemia, autoimmune or immune-mediated skin diseases including bullous skin diseases, erythema multiforme and atopic and contact dermatitis, psoriasis, neutrophilic dermatoses, cystic fibrosis, allergic diseases such as asthma, allergic rhinitis, food hypersensitivity and urticaria, cystic fibrosis, immunologic diseases of the lung such as eosinophilic pneumonia, idiopathic pulmonary fibrosis, adult respiratory disease (ARD), acute respiratory distress syndrome (ARDS) and inflammatory lung injury such as asthma, chronic obstructive pulmonary disease (COPD), airway hyper-responsiveness, chronic bronchitis, allergic asthma and hypersensitivity pneumonitis, transplantation associated diseases including graft and organ rejection and graft-versus-host-disease, septic shock, multiple organ failure, obesity, type 2 diabetes, non alcoholic liver cirrhosis, non alcoholic liver disease, oncology (tumor angiogenesis, primary tumors and metastases).

Among the autoimmune and chronic inflammatory disease, preferred diseases are: Rheumatoid Arthritis, Multiple Sclerosis, Systemic Lupus Erythematosus, inflammatory bowel diseases, Crohn's diseases, psoriasis, ulcerative colitis, atopic dermatitis.

Examples of cell proliferation disorders or cancers include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

Typically, the composition of the present invention are useful for the prevention or treatment of breast cancer, colon cancer, gastric cancer, glioma, hepatocellular carcinoma, kidney cancer, leukemia, lung cancer, lymphoma, melanoma, multiple myeloma, ovarian cancer, pancreatic cancer, prostate cancer.

Advantageously, the treatment is for:
targeting and/or killing the cancer cells or the cells at increased risk for becoming cancerous;
increasing the effectiveness of a therapeutic agent, advantageously a chemotherapeutic agent; and/or
preventing tumor metastasis.

The invention also relates to pharmaceutical compositions comprising antagonists as defined above. Therefore, said antagonists may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of antagonists may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Antagonists of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antagonists of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the present invention, and such particles may be easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

The invention also provides kits comprising the antagonists of the invention. Kits containing antagonists of the invention find use in diagnostic and therapeutic assays.

Diagnostics

The invention further provides a diagnostic method useful during diagnosis of IL-17-mediated diseases such as neoplastic disorders, including solid tumors, which involves measuring the expression level of IL-17 protein or transcript in tissue or other cells or body fluid from an individual and comparing the measured expression level with a standard IL-17 expression level in normal tissue or body fluid, whereby an increase in the expression level compared to the standard is indicative of a disorder.

Anti-IL-17 antibodies and antigen-binding fragments, variants, and derivatives thereof, can be used to assay IL-17 protein levels in a biological sample using classical immunohistological methods known to those of skill in the art (e.g., see Jalkanen, et al., *J. Cell. Biol.* 101:976-985 (1985); Jalkanen et al., *J. Cell Biol.* 105:3087-3096 (1987)). Other antibody-based methods useful for detecting IL-17 protein expression include immunoassays, such as the enzyme linked immunosorbent assay (ELISA), immunoprecipitation, or Western blotting. Suitable assays are described in more detail elsewhere herein.

By "assaying the expression level of IL-17 polypeptide or isoform" is intended qualitatively or quantitatively measuring or estimating the level of IL-17 polypeptide in a first biological sample either directly (e.g., by determining or estimating absolute protein level) or relatively (e.g., by comparing to the disease associated polypeptide level in a second biological sample). Preferably, IL-17 polypeptide expression level in the first biological sample is measured or estimated and compared to a standard IL-17 polypeptide level, the standard being taken from a second biological sample obtained from an individual not having the disorder or being determined by averaging levels from a population of individuals not having the disorder. As will be appreciated in the art, once the "standard" IL-17 polypeptide level is known, it can be used repeatedly as a standard for comparison.

By "biological sample" is intended any biological sample obtained from an individual, cell line, tissue culture, or other source of cells potentially expressing IL-17. Methods for obtaining tissue biopsies and body fluids from mammals are well known in the art.

The anti-IL-17 antibodies for use in the diagnostic methods described above in this section are intended to include those anti-IL-17 antibodies, or fragments, variants, or derivatives that are described in detail elsewhere herein as if they were separately listed in this section.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Ha112003); Harlow and Lane (1988) Antibodies: A Laboratory Manual (Cold Spring Harbor Press); Dieffenbach and Dveksler (2003) PCR Primer (Cold Spring Harbor Press).

The invention will further be illustrated in view of the following examples, which are not intended to be limiting.

EXAMPLES

Figure 1A:
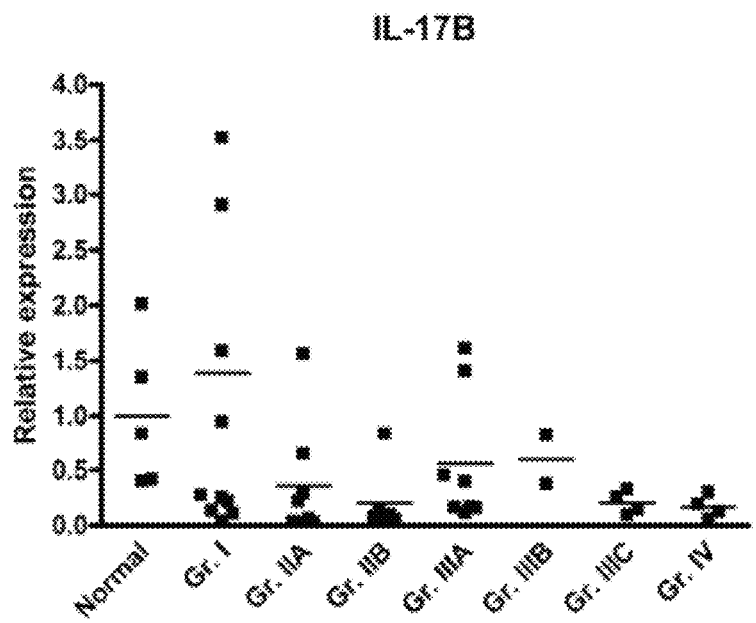
FIGS. 1A-1L: A-E. Expression of IL-17B, IL-17C, IL-17D, IL-17RB (receptor of IL-17B) and IL-17RE (receptor of IL-17C) in human breast cancer biopsies. mRNA expression of IL-17B, IL-17C, IL-17D, IL-17RB and IL-17RE was analyzed by RT-QPCR in normal breast biopsies (normal) and breast tumors of various grades (from grade I to IV). F-L. Coexpression data in 3 human breast cancer biopsies.
Figure 1B:
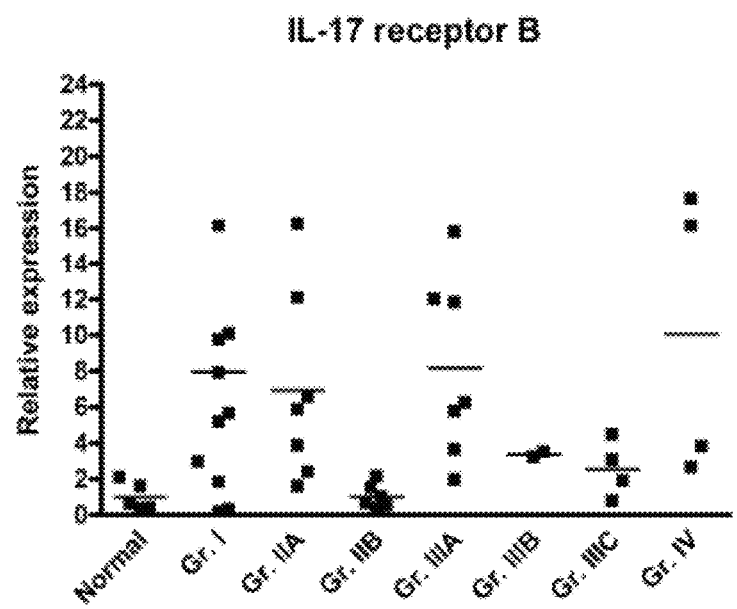
Figure 1C:
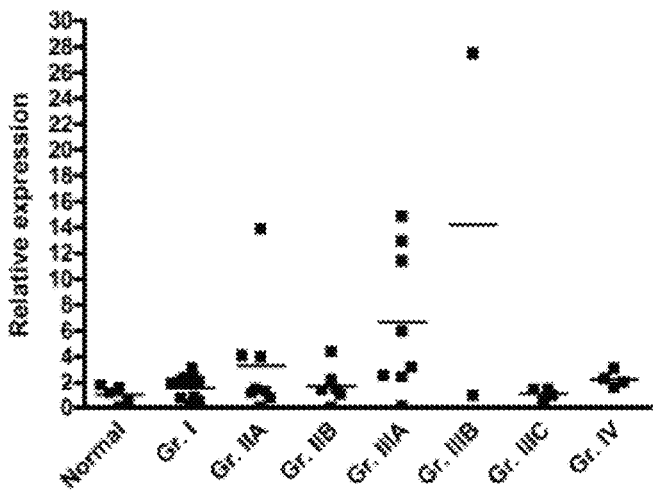
Figure 1D:
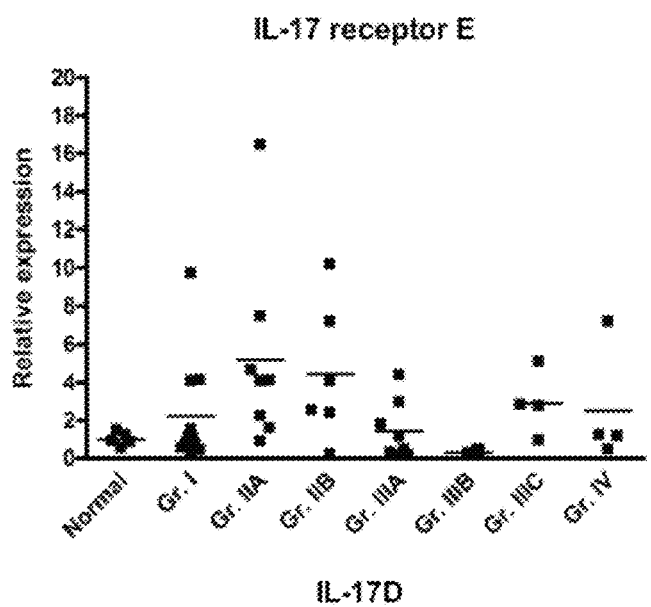
Figure 1E:
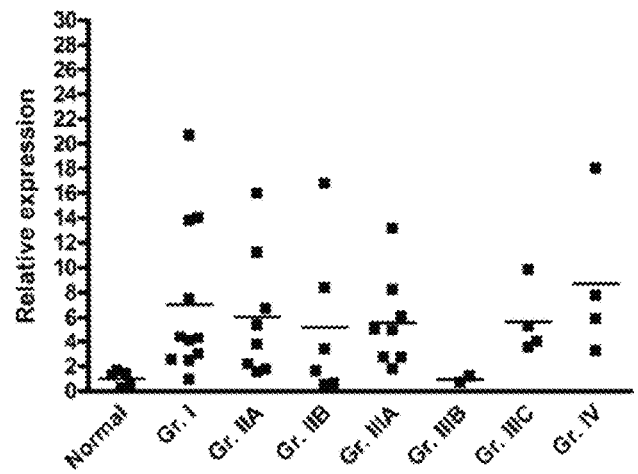
Figure 1F:
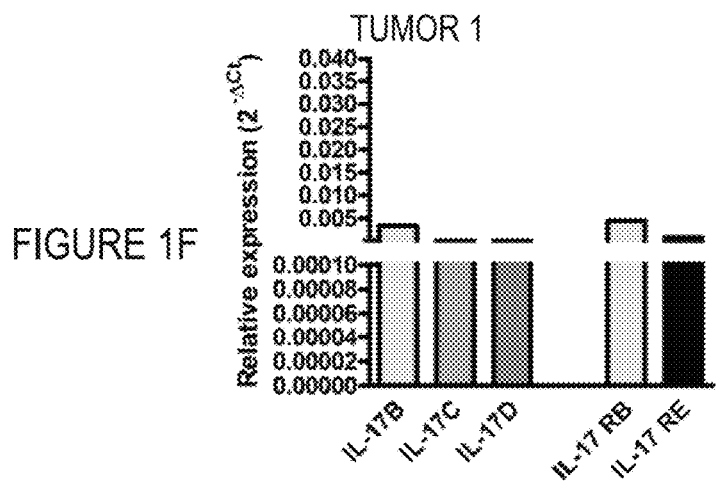
Figure 1G:
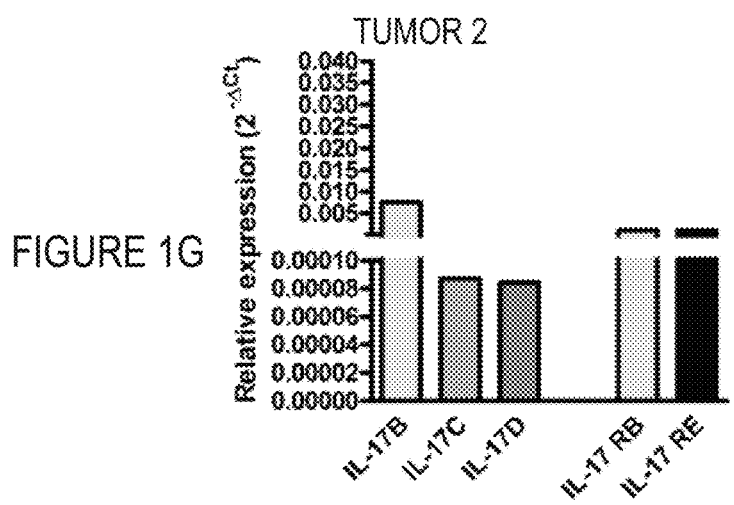
Figure 1H:
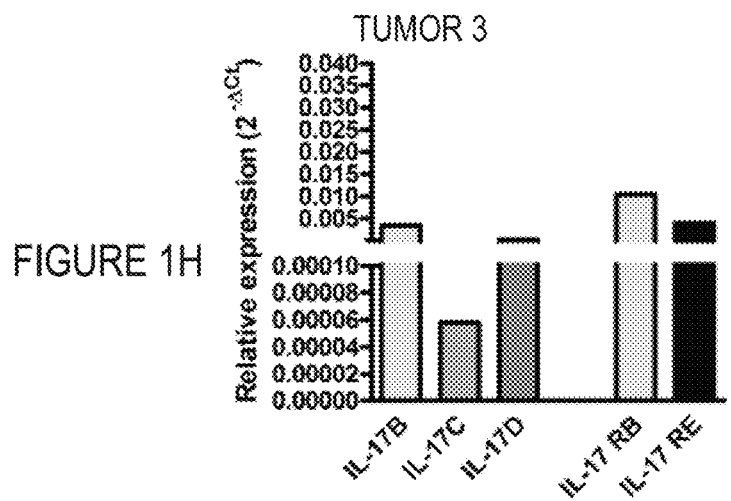
Figure 1I:
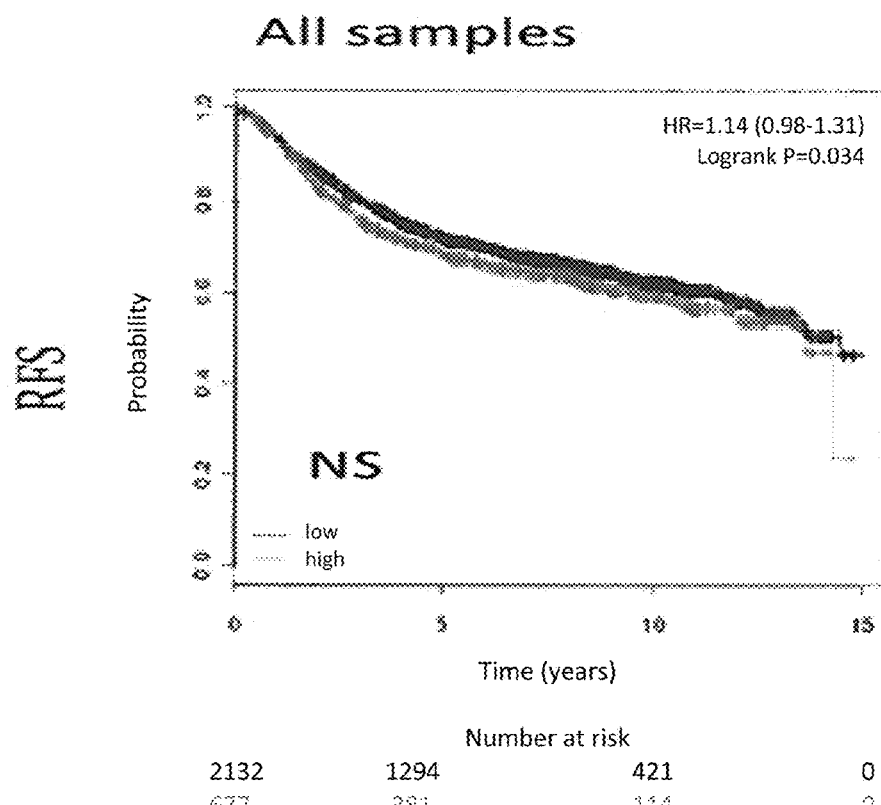
Figure 1J:
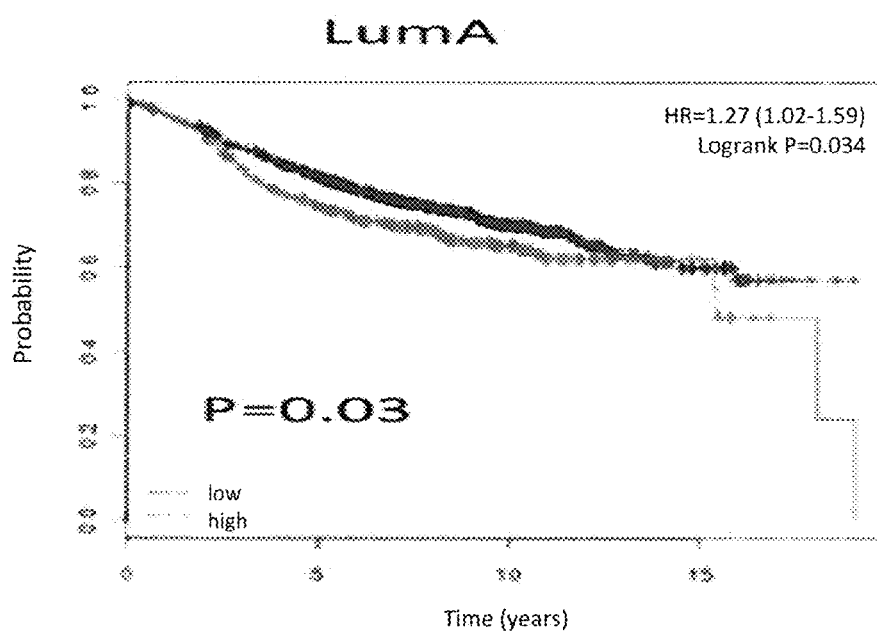
Figure 1K:
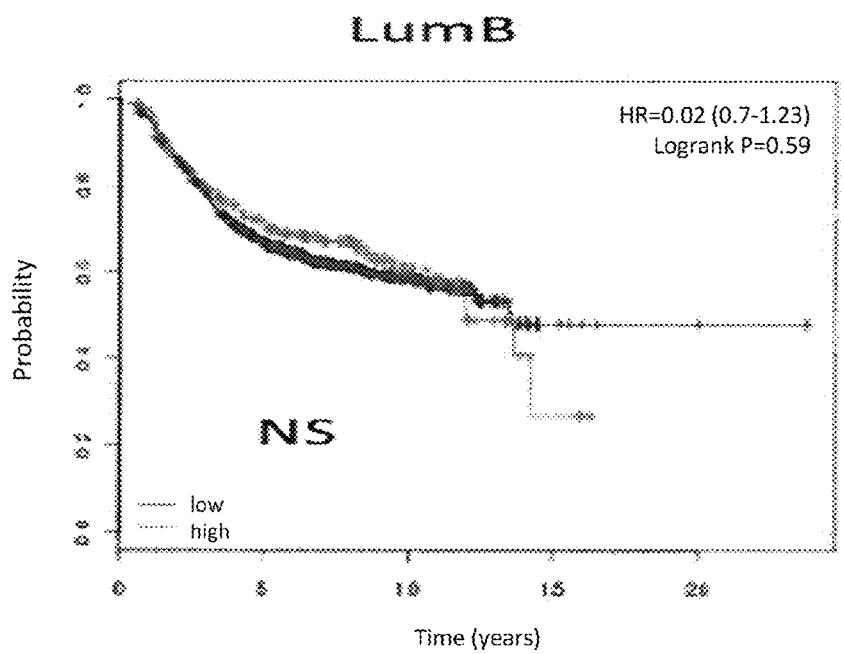
Figure 1L:
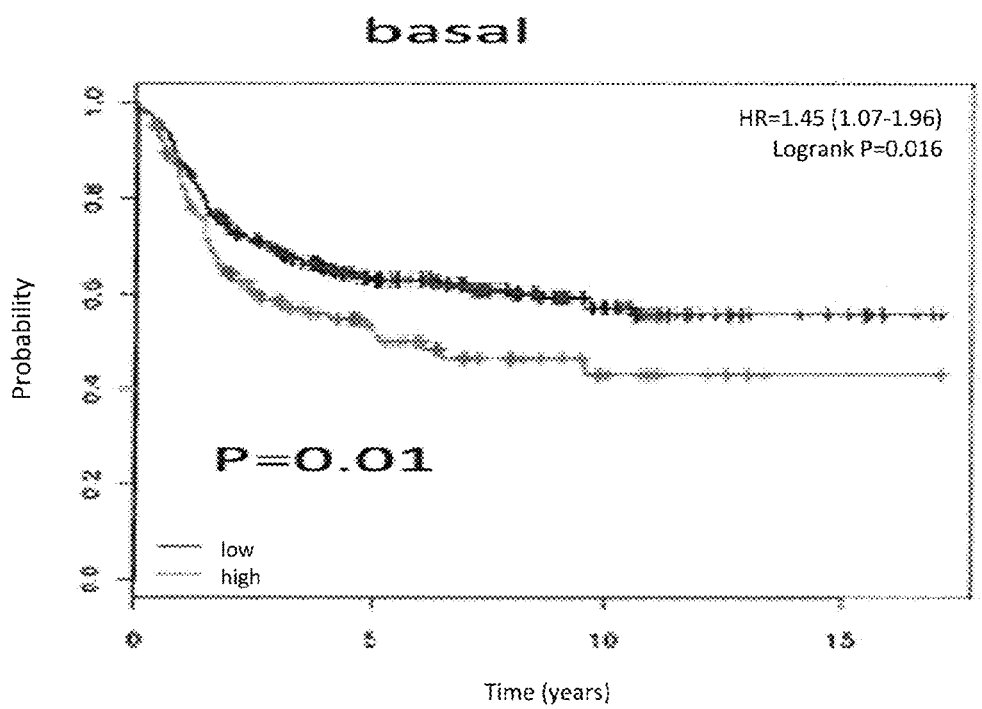

Experimental Procedures
Cell Culture

HCT116, HT29, and SKOV3 cell lines were cultured in McCoy5a medium (Life technologies) supplemented with 10% FCS, 2% glutamine and 1% antibiotics (Life technologies). MCF7, T47D, MDA-MB231 and BT20 cell lines were cultured in RPMI 1640 medium supplemented as described above. SKMEL5, LOVO, OAW42, MDA-MB435S, MDA-MB436, MDA-MB468 cell lines and normal human dermal fibroblasts (NHDF) were grown in DMEM/F12 medium (Life Technologies) supplemented as described above. MCF10A cell line was maintained in DMEM/F12 medium (Life Technologies) supplemented as described above and with 10 µg/ml insulin, 0.5 µg/ml hydrocortisone, 20 ng/ml EGF and 100 ng/ml cholera toxin. MDA-MB157 cell line was cultured in DMEM medium (Life technologies) supplemented with 10% FCS, 2% glutamine and 1% antibiotics. All cells were kept at 37° C. in 5% CO2 atmosphere incubator.

Cell Proliferation Assay ([3H]-TdR)

400 cells are seeded per well in 96 well plate (Corning) and kept overnight in adequate complete medium. Medium is then removed and replaced with adequate complete medium supplemented with 0 to 100 ng/ml of cytokines as indicated. Each condition is performed in triplicate. After 72 h of culture, cells were pulsed for 16 h with tritiated thymidine ([3H]-TdR) (0.5 µCi) and harvested. [3H]-TdR uptake was measured using PerkinElmer microβ 2 2450 microplate counter.

mRNA Extraction and cDNA Synthesis

Total RNA was isolated using the GenElute™ Mammalian Total RNA kit (Sigma-Aldrich, St. Louis, Mo.) following the manufacturer's instructions. Total RNA (1 µg) was treated with 1 U/µg RNA of DNase I Amplification Grade (Invitrogen) according to the manufacturer's instructions, and in the presence of 10 U/µg RNA of RNaseOUT (Invitrogen). After DNase inactivation, RNA was reverse transcribed using random nonamers (Promega, Madison, Wis.) and M-MLV Reverse Transcriptase H Minus (Promega) according to the manufacturer's instruction.

Breast, Pancreas and Colon Cancer cDNA Samples

Ready to use normal breast and breast cancer cDNA samples (FIGS. 1A-1L), normal pancreas and pancreatic cancer cDNA samples (FIGS. 3A-3I) and normal colon and colon cancer cDNA samples (FIG. 4) were purchased at ORIGENE.

Quantitative Polymerase Chain Reaction of Reverse Transcribed mRNA (RT-QPCR)

The forward and reverse primers used in the PCR reaction were designed with Primer-BLAST software (http://www.ncbi.nlm.nih.gov/tools/primer-blast/), except for GAPDH (Mayer et al., 2002). Real-time polymerase chain reaction quantification was carried out with the LightCycler 480 II System (Roche Diagnostics) using the SYBR Premix Ex Taq (Tli RNaseH Plus) kit (Ozyme). The cycling conditions were as follows: 95° C. for 1 min followed by 40 cycles of 95° C. for 20 s, 60° C. for 20 s and 72° C. for 30 s. The sizes of the RT-PCR products were confirmed by agarose electrophoresis. At the end of the amplification, a melting temperature analysis of the amplified gene products was performed routinely for all cases; the PCR products were melted by gradually increasing the temperature from 60 to 95° C. in 0.3° C. steps, and the dissociation curves were generated with the Melting Curve analysis tool of the LightCycler 480 software (Roche Diagnostics). We confirmed that only one product was consistently amplified in all PCR reactions. The negative water control showed no amplification. The relative expression of the genes of interest normalized to GAPDH or ACTIN, was determined by the delta Ct method.

| Gene and GenBank accession | Primer sequence |
|---|---|
| IL17B # NM_014443.2 | 5'-GCCACTGGACCTGGTGTCACG-3' (SEQ ID NO: 1) 5'-CTGGGGTCGTGGTTGATGCTGT-3' (SEQ ID NO: 2) |
| IL17C # NM_013278.3 | 5'-TGCCAAGTGGGGGCAGGCTT-3' (SEQ ID NO: 3) 5'-CGTGTCCACACGGTATCTCCAGGG-3' (SEQ ID NO: 4) |

-continued

| Gene and GenBank accession | Primer sequence |
|---|---|
| IL17D # NM_138284.1 | 5'-GCCCTGGGCCTACAGAATCTCCT-3'<br>(SEQ ID NO: 5)<br>5'-CCTCGGTGTAGACGGAACGGC-3'<br>(SEQ ID NO: 6) |
| IL17RB # NM_018725.3 | 5'-TACCCCGAGAGCCGACCGTT-3'<br>(SEQ ID NO: 7)<br>5'-GGCATCTGCCCGGAGTACCCA-3'<br>(SEQ ID NO: 8) |
| IL17RE # NM_153480.1 | 5'-CCACCTTCAGGCCATGCAGCC-3'<br>(SEQ ID NO: 9)<br>5'-CTGTCATCCGTGTGGGAGGCCA-3'<br>(SEQ ID NO: 10) |
| GAPDH | 5'-GAAGGTGAAGGTCGGAGTCA-3'<br>(SEQ ID NO: 11)<br>5'-GACAAGCTTCCCGTTCTCAG-3'<br>(SEQ ID NO: 12) |
| ACTIN | 5'-CAGCCATGTACGTTGCTATCCAGG-3'<br>(SEQ ID NO: 13)<br>5'-AGGTCCAGACGCAGGATGGCATG-3'<br>(SEQ ID NO: 14) |

Migration Assay 20,000 cells were seeded on the upper chamber of transwell chambers in 1% FCS adequate medium alone (medium) or supplemented with recombinant human IL-17B (100 ng/ml) for 22 hours at 37° C. as indicated. The cells on the transwell were stained with 0.5% crystal violet prior imaging and enumeration. The number of cells migrated onto the transwell were counted (magnification ×4). The graph presents data after quantification in % of cell migration compared to non-treated cells. Results are the mean +/− SEM of two independent experiments, each performed in triplicate.

Matrigel Invasion Assay

Cells were cultured in adequate complete medium supplemented with 100 ng/ml of recombinant cytokines for 2 days (MDA-MB231) or 14 days (OAW42). Matrigel Invasion Chambers (BD BioCoat™ BD Matrigel™ Invasion Chamber, 24-well Cell culture inserts) were then used to study the invasiveness of cancer cells. $2.10^4$ cells are then added to the upper compartment of the chambers in 1% FCS adequate medium alone or supplemented with 100 ng/ml of recombinant cytokines as indicated. Medium supplemented with 10% FCS is added to the lower wells of the chambers. Plates are incubated for 22 hours at 37° C. Transwell filters are then fixed and stained in Giemsa solution following which non-invading cells are removed from the upper surface of the transwell membrane using a cotton swab. Images of cells from three representative fields are captured digitally and the number of cells present on the transwell is counted.

IL-6 ELISA

Normal human dermal fibroblasts (NHDF) were cultures in complete medium alone or supplemented with 30 ng/mlL of recombinant IL-17B, IL17C or IL17D as indicated. After 16 h of culture, supernatant are collected. IL-6 ELISA is performed with human IL-6 development kit (Peprotech) following manufacturer's instructions.

Cytotoxicity Assay

Cells were seeded in a 96 wells plate (1000 cells/well) in adequate complete medium alone (medium) or treated with recombinant human IL-17B at 1 or 10 ng/ml as indicated. After 48 h of culture, medium was changed to a FCS-free one supplemented with corresponding concentration of cytokines After 24 h, culture medium is then further supplemented with docetaxel at 5, 10, 20 or 40μg/ml or doxorubicin at 20 or 30 μM as indicated. Untreated cells (control medium) and Triton X100 treated cells (100% cell death) were used as controls. Each condition was performed in duplicates. The percentage of cell death (=cytotoxicity) was determined after 7 h of culture in the presence of docetaxel or doxorubicin using the Cytotoxicity Detection Kit (Roche) according to the manufacturer's instructions. To this aim, 100 μl of supernatant from each well were collected into a 96 wells plate and incubated with 100 μl of freshly prepared Reaction Mixture for 30 minutes at room temperature. Optical density was then read at 490 nm. The percentage of cytotoxicity is calculated as followed: %=100×(exp value−control medium value)/(Triton X100 treated cells value−control medium value)

Gene Expression Profiling 285 primary breast carcinoma samples from the CIT dataset were analyzed for expression profiling on Affymetrix U133-Plus2.0 chips (Guedj M, A refined molecular taxonomy of breast cancer, Oncogene (2012) 31, 1196-1206). Normal colon, colon carcinoma and metastasis samples from (Del Rio M, Gene Expression Signature in Advanced Colorectal Cancer Patients Select Drugs and Response for the Use of Leucovorin, Fluorouracil, and Irinotecan, JOURNAL OF CLINICAL ONCOLOGY, 2007) were analyzed for expression profiling on Affymetrix U133 chips.

Results

Example 1

IL-17 Isoforms and their Receptors are Expressed in Human Cancers

Figure 2:
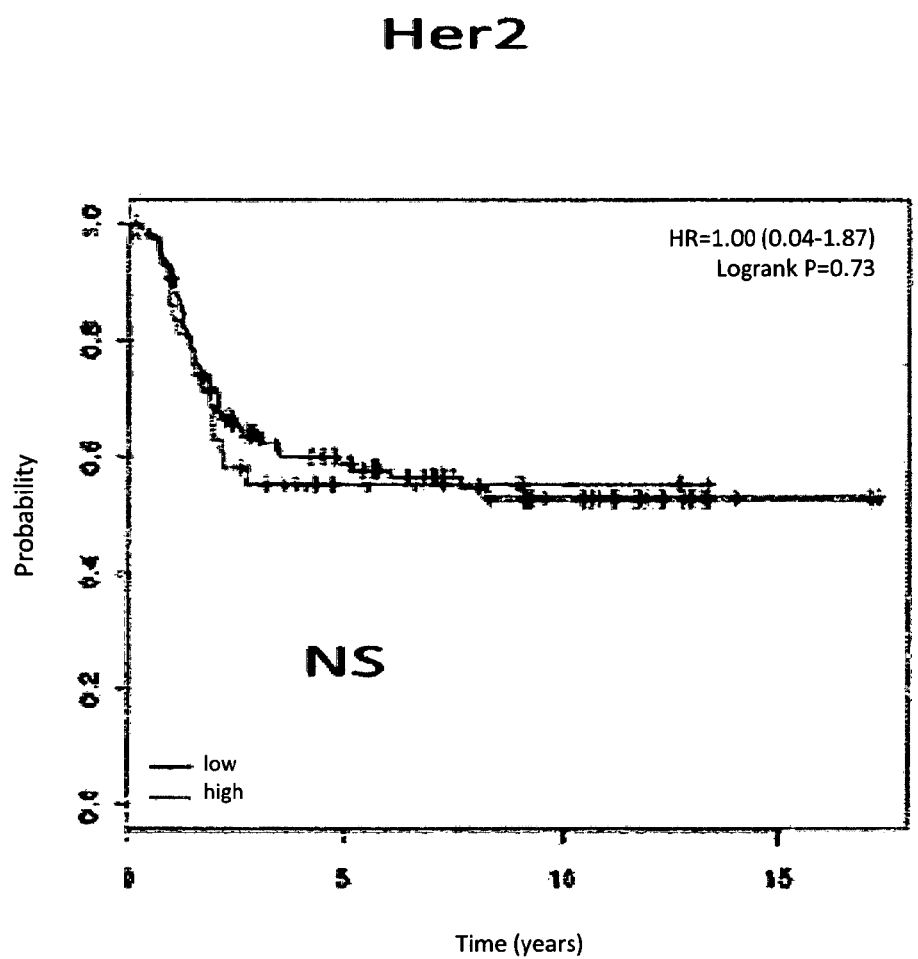
FIG. 2: High expression of IL-17B predicts a poorer relapse free survival (RFS) in patients with breast cancer. Expression of IL-17B in a cohort of 285 primary breast carcinoma samples was analyzed on Affymetrix chips. In the basal-like subgroup, high expression of IL-17B (grey line) was significantly associated with a poorer RFS.
Figure 3A:
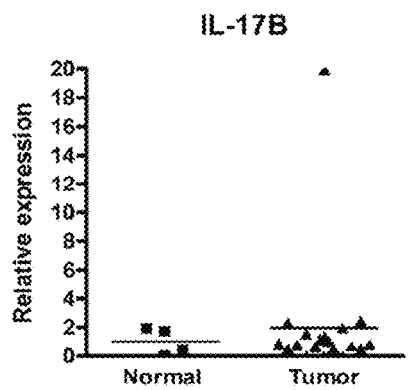
FIGS. 3A-3I: A-E. Expression of IL-17B, IL-17C, IL-17D, IL-17RB (receptor of IL-17B) and IL-17RE (receptor of IL-17C) in human pancreatic cancer biopsies. F-I. mRNA expression of IL-17B, IL-17C, IL-17D, IL-17RB and IL-17RE was analyzed by RT-QPCR in normal pancreas biopsies (normal) and pancreatic tumors.
Figure 3D:
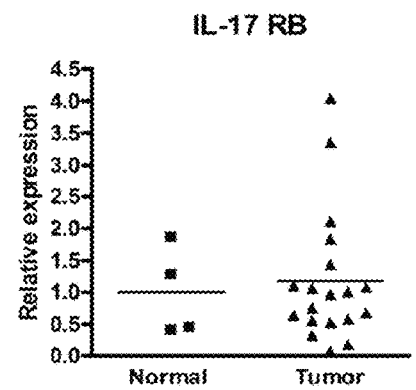
Figure 3B:
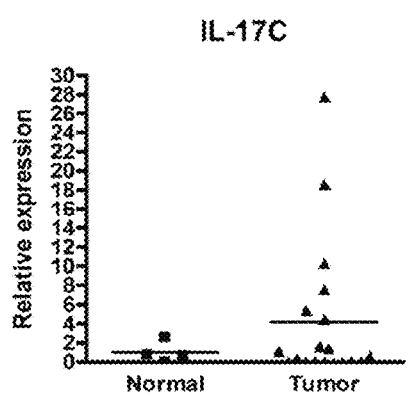
Figure 3E:
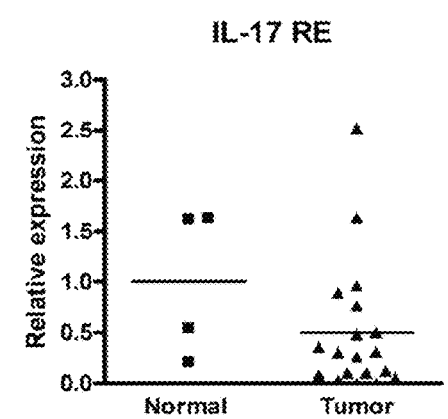
Figure 3C:
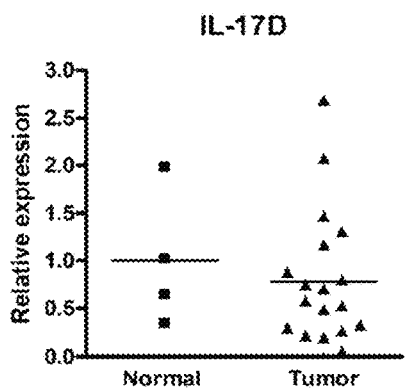
Figure 3F:
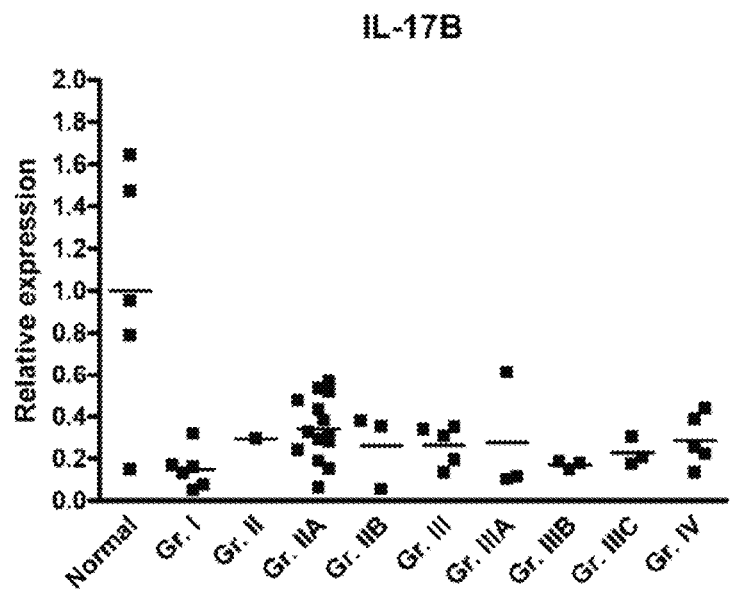
Figure 3G:
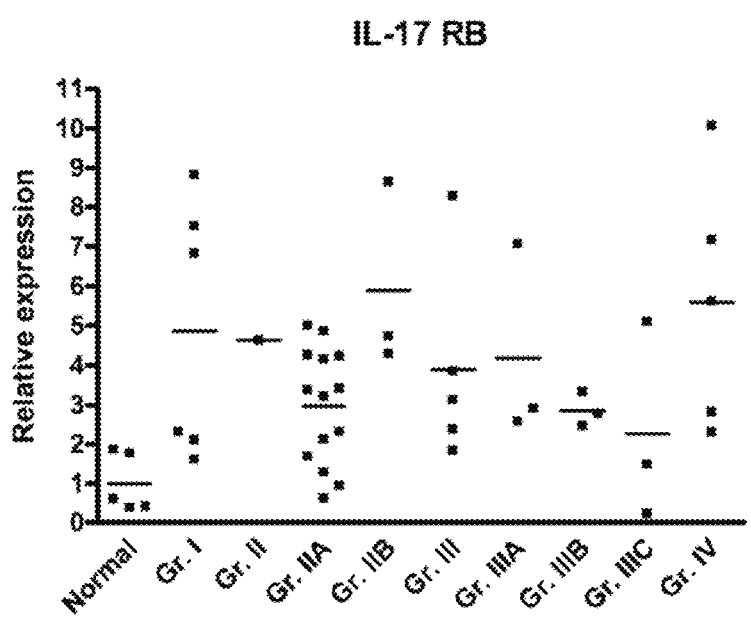
Figure 3H:
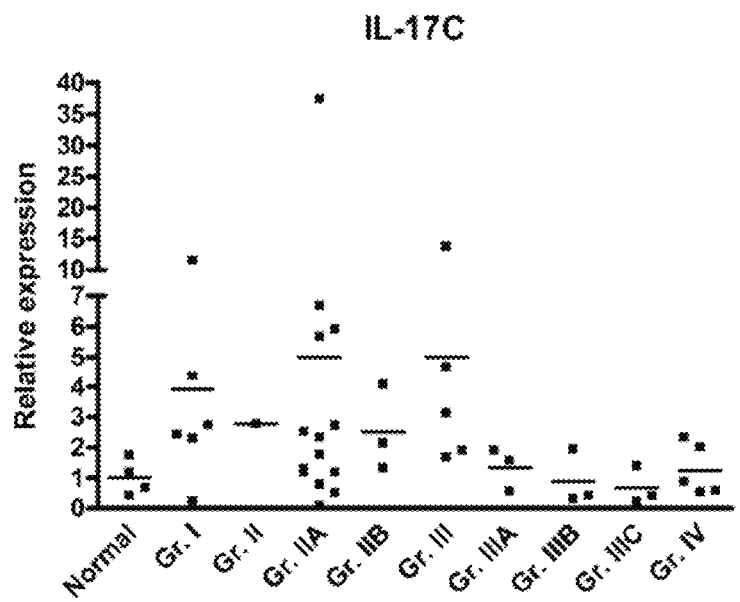
Figure 3I:
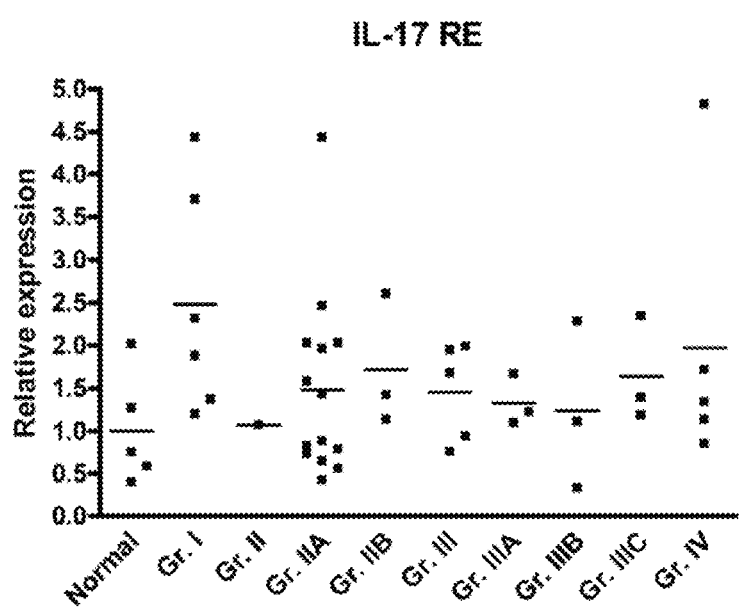
Figure 4:
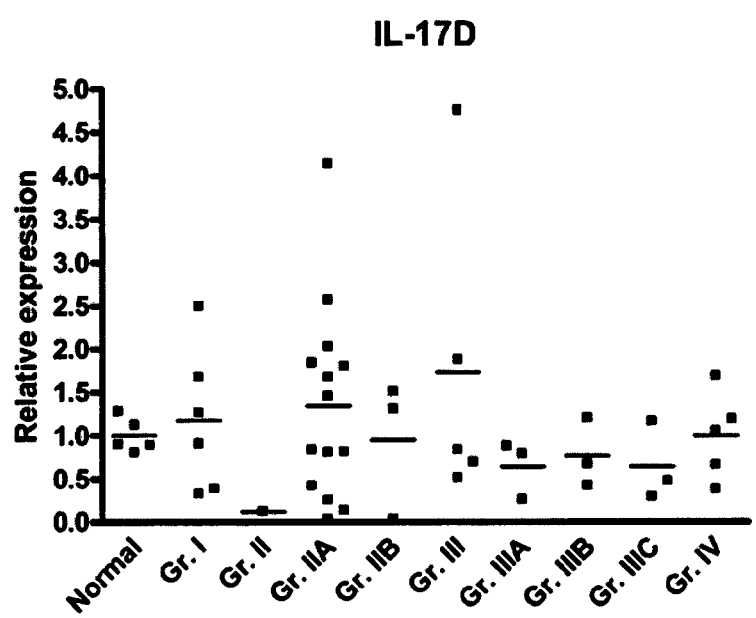
FIG. 4: Expression of IL-17B, IL-17C, IL-17D, IL-17RB (receptor of IL-17B) and IL-17RE (receptor of IL-17C) in human colon cancer biopsies. mRNA expression of IL-17B, IL-17C, IL-17D, IL-17RB and IL-17RE was analyzed by RT-QPCR in normal colon biopsies (normal) and colon tumors.
Figure 5:
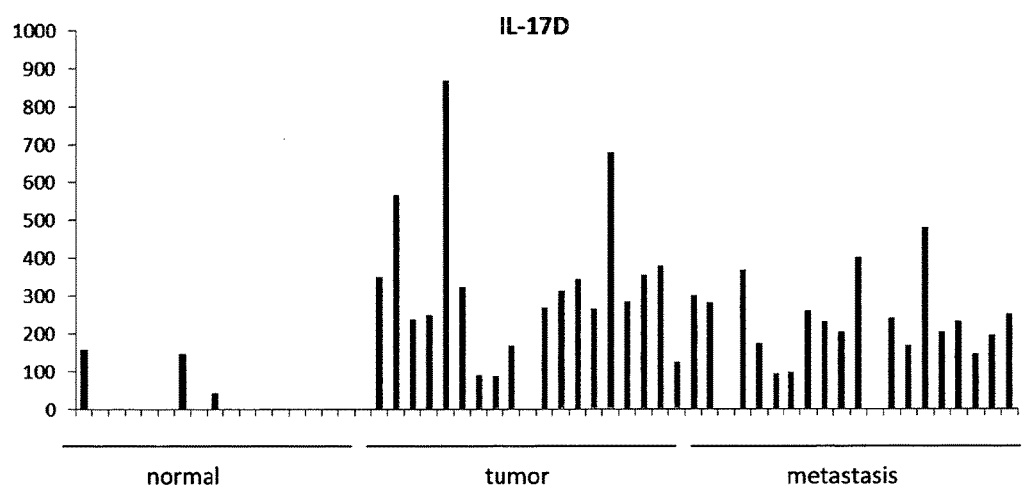
FIG. 5: Expression of IL-17D in human normal colon, primary colon cancer and colon cancer metastasis. Expression of IL-17D in biopsies of normal colon, primary colon cancer and metastasis of colon cancer was analyzed on Affymetrix chips.
Figure 6A:
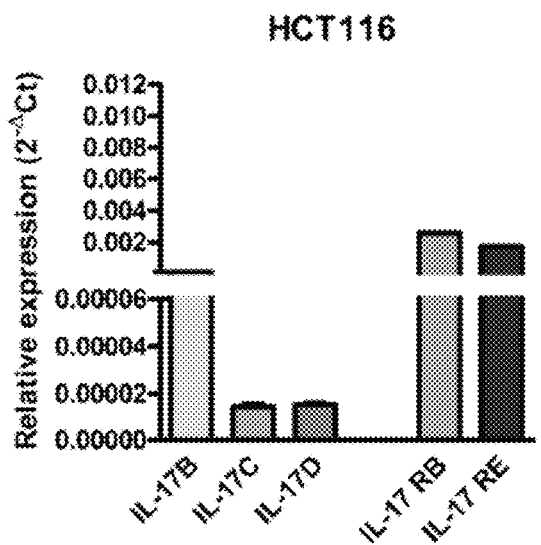
FIGS. 6A-6O: Expression of IL-17B, IL-17C, IL-17D, IL-17RB (receptor of IL-17B) and IL-17RE (receptor of IL-17C) in human cancer cell lines. mRNA: (A-C)=colon; (D-L)=breast; (M)=melanoma; (N-O)=ovary. Expression of IL 17B, ID 17C, ID 17D, IL17E and IL17F was analyzed by RT-QPCR in various human cell lines.
Figure 6B:
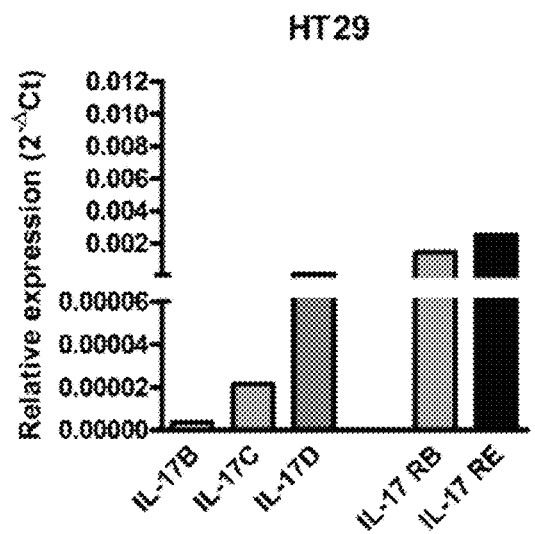
Figure 6C:
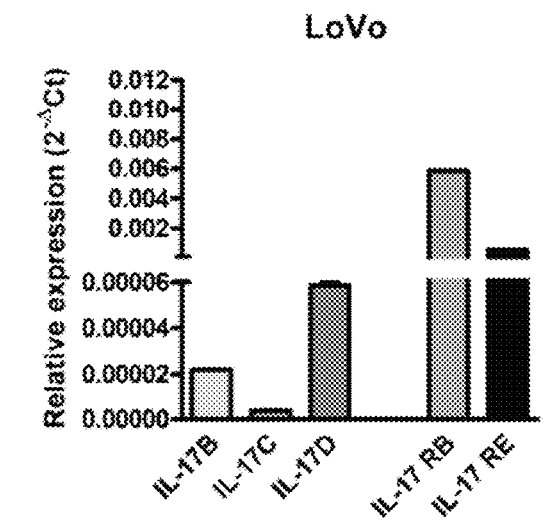
Figure 6D:
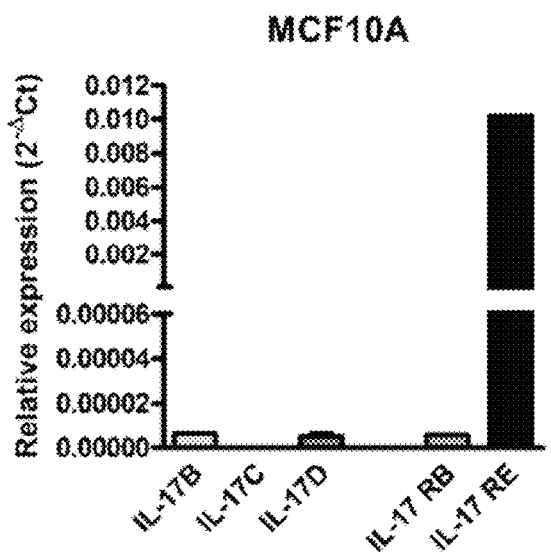
Figure 6E:
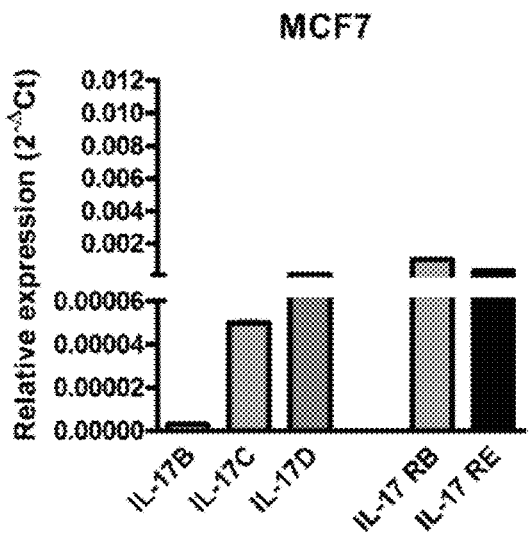
Figure 6F:
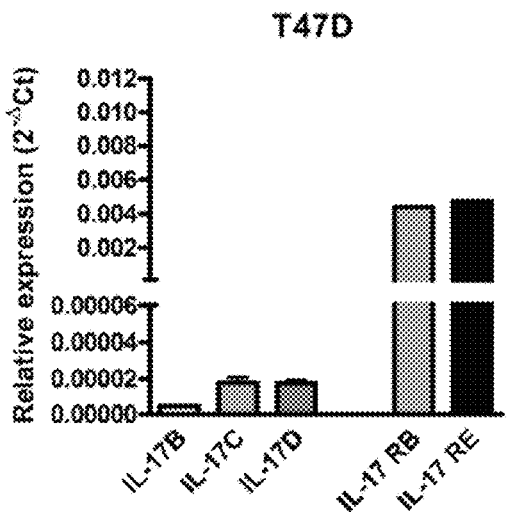
Figure 6G:
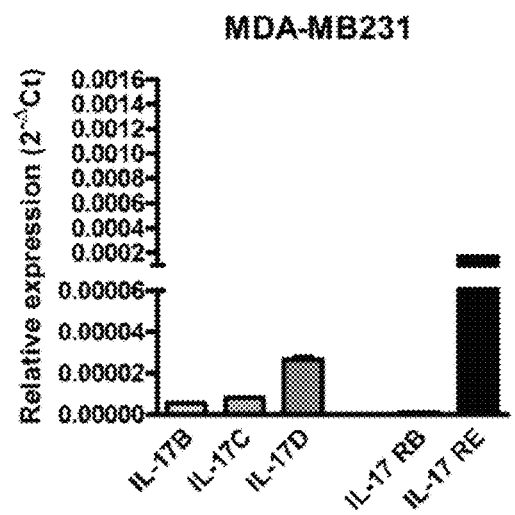
Figure 6H:
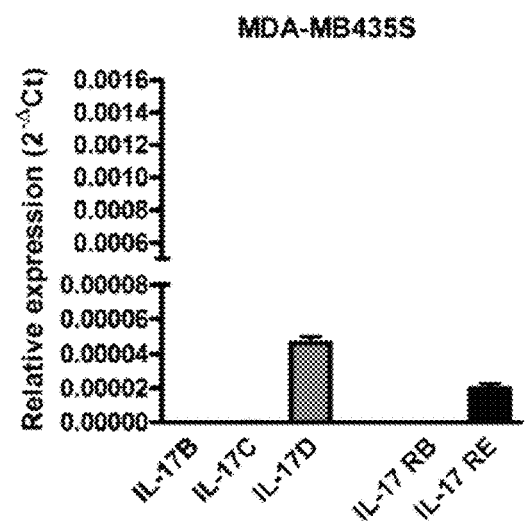
Figure 6I:
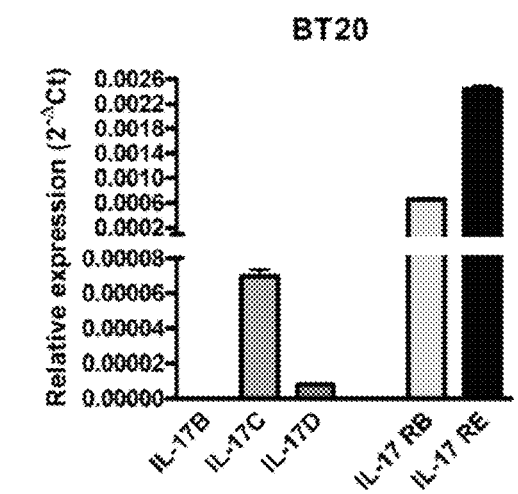
Figure 6J:
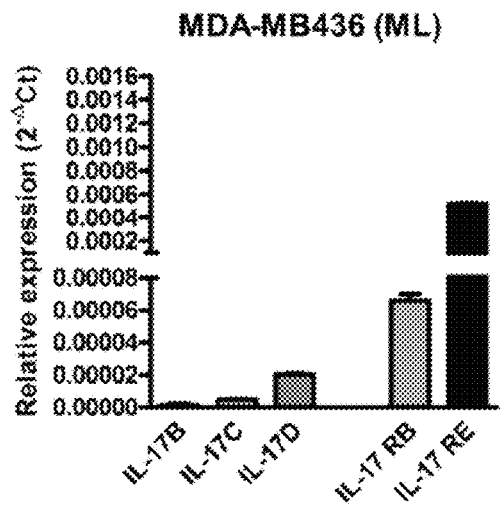
Figure 6K:
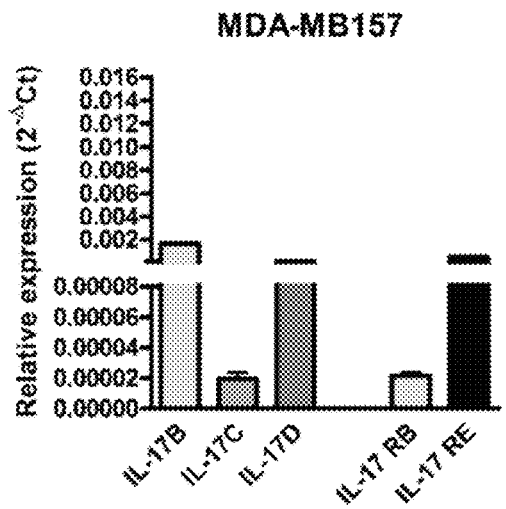
Figure 6L:
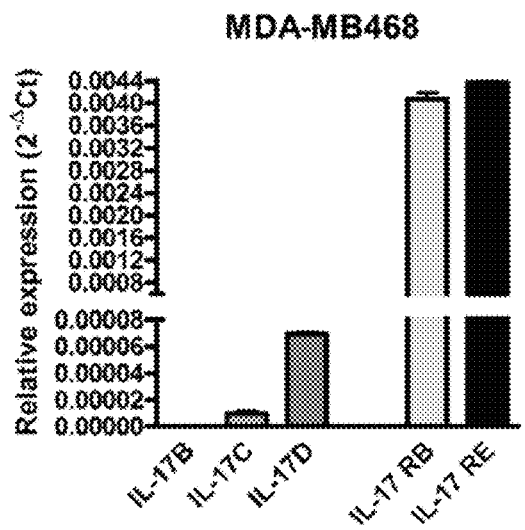
Figure 6M:
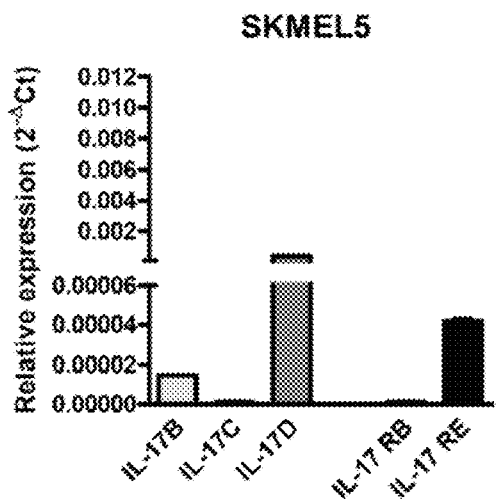
Figure 6N:
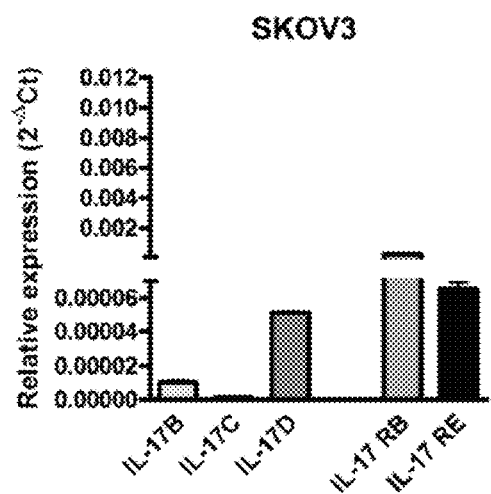
Figure 6O:
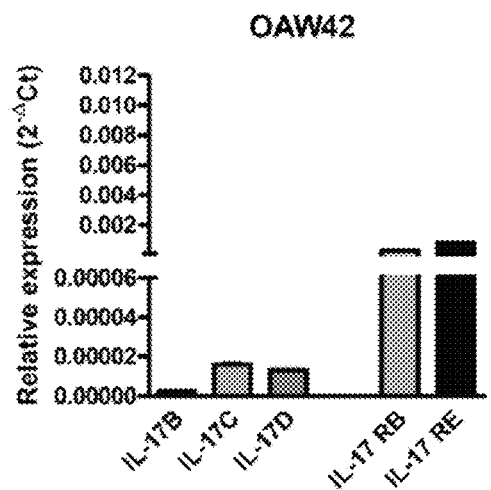
Figure 7A:
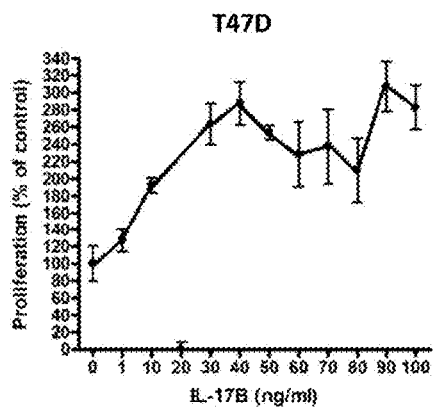
FIGS. 7A-7D: IL-17B increases the proliferation of breast cancer cells. T47D (A), MCF7 (B), MDA-MB436 (C) and MDA-MB468 (D) cells were cultured in adequate complete medium supplemented with increasing doses of recombinant human IL-17B as indicated. Cell proliferation was assessed at 72 h using tritiated thymidine ([3H]-TdR) incorporation protocol.
Figure 7B:
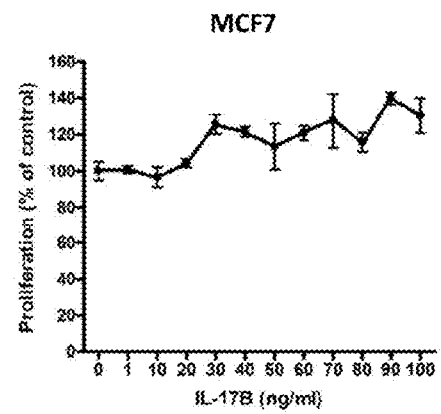
Figure 7C:
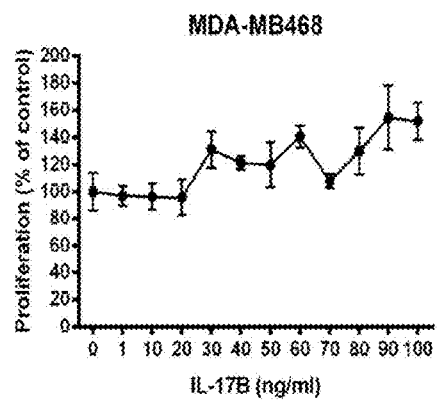
Figure 7D:
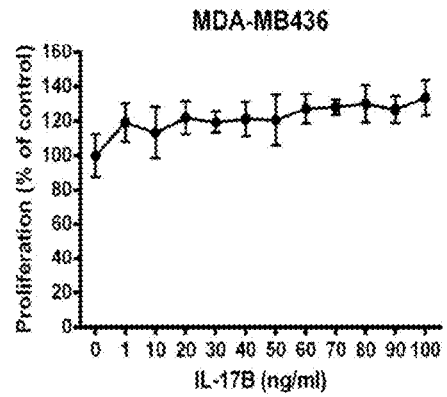

IL-17A and IL-17A producing cells (e.g., Th17 cells) are increased in human cancers. However, the expression of other IL-17 isoforms (in particular, IL-17B, IL17C and IL17D) is not known. We therefore analyzed the expression of IL-17B, IL17C and IL17D as well as the expression of their receptors (IL-17RB, the receptor of IL-17B and IL-17RE, the receptor of IL-17C) by RT-QPCR in various human cancer biopsies and cancer cell lines. As shown in FIGS. 1A-1E, IL-17B, IL-17C and IL-17D were upregulated in some breast cancer biopsies compared to normal breast. Furthermore, both IL-17RB and IL-17RE were upregulated in some breast cancer biopsies compared to normal breast. High expression of IL-17B was significantly associated with a poorer RFS (Relapse Free Survival), especially in the basal-like subgroup (FIG. 2). As shown in FIGS. 3A-3I, IL-17B, IL-17C, IL-17D, IL-17RB and IL-17RE were expressed in some pancreatic cancer biopsies. In some cancer cases, IL-17C and IL-17B were upregulated compared to normal pancreas. As illustrated in FIG. 4, IL-17C, IL-17D, IL-17RB and IL-17RE were upregulated in some colon tumors, suggesting that they may be involved in colon cancer progression. IL-17D upregulation in some colon cancers (primary tumors and metastasis) compared to normal colon was further exemplified in FIG. 5. As shown in FIGS. 6A-6O, the human cancer cell lines tested expressed one or several of the following genes: IL-17B, IL-17C, IL-17D, IL-17RB and IL-17RE. Interestingly, the non-cancerous cell line MCF10A did not express IL-17B, IL-17C, IL-17 D or IL-17RB (however, it expressed IL-17RE). In aggregates, this suggests that IL-17B, IL-17C, IL-17D, IL-17RB and IL-17RE are expressed and/or upregulated in human cancers and cancer cell lines, suggesting that they may be therapeutic target for the treatment of cancer.

As exemplified in FIGS. 1 F-1L, several breast cancer biopsies expressed two or more IL-17 isoforms. Along similar lines, as shown in FIGS. 6A-6O, some cancer cell lines expressed several IL-17 isoforms: MCF7 expressed IL-17C and IL-17D and MDA-MB157 express IL-17B and IL-17D. Altogether this suggests that, in some cases, targeting two or more isoforms or their receptors simultaneously may be required for the treatment of cancer.

In conclusion, all IL-17 isoforms and their receptors are upregulated in human cancers. Targeting one isoform or receptor or several isoforms simultaneously or several receptors simultaneously may be therapeutic options for the treatment of cancer.

Example 2

IL-17B and IL-17RB Stimulate Cancer Cell Proliferation

As IL-17B and IL-17RB are upregulated in human cancers (Example 1), we tested whether they may have oncogenic properties. We first tested whether IL-17B would alter the proliferation of human cancer cells that express IL-17RB. As shown in FIGS. 7A-7D, IL-17B increased T47D, MCF7, MDA-MB436 and MDA-MB468 breast cancer cell proliferation. Interestingly, IL-17B did not stimulate the proliferation of the MDA-MB231 cells that do not express IL-17RB (data not shown). Therefore, IL-17B and IL-17RB can promote tumor growth by increasing cancer cell proliferation.

Example 3

IL-17B and IL-17RB Increase Cancer Cell Migration and Invasion

Figure 8A:
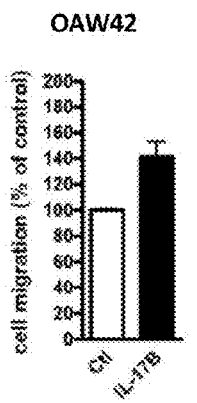
FIGS. 8A-8C: IL-17B increases migration and invasion of breast and ovarian cancer cells. OAW42 (ovarian, A) and MCF7 (breast, B) cells were cultured in complete adequate complete medium alone (Ctl) or supplemented with 100 ng/ml of recombinant human IL-17B (IL-17B) as indicated. Cell migration was evaluated in transwell migration assay. (C) OAW42 cells were cultured for 14 days in adequate complete medium alone (Ctl) or supplemented with 100 ng/ml of recombinant human IL-17B (IL-17B) as indicated. Cell invasiveness was then evaluated in Matrigel Invasion Chambers.
Figure 8B:
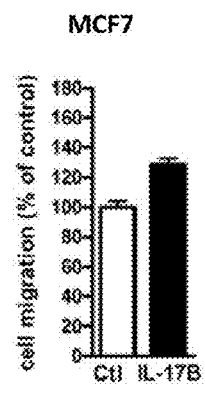
Figure 8C:
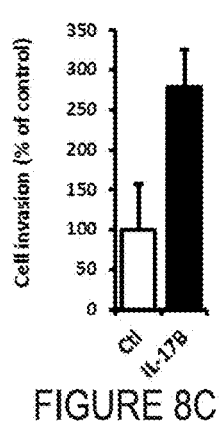
Figure 11A:
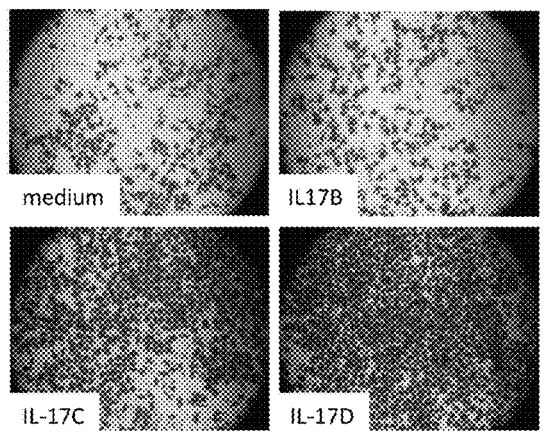
FIGS. 11A-11B: IL-17C and IL-17D increase invasion of MDA-MB231 breast cancer cells. MDA-MB231 were cultured for 2 days in complete adequate medium alone (medium) or supplemented with 100 ng/ml of recombinant human IL-17B, IL-17C or IL-17D as indicated. Cell invasiveness was then evaluated in Matrigel Invasion Chambers (A, representative photomicrographs, B, quantification).
Figure 11B:
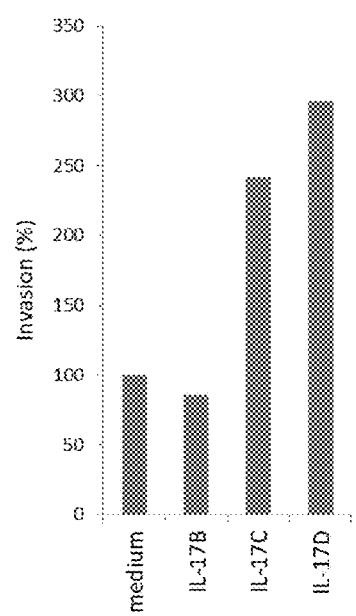

We tested whether IL-17B may increase migration and invasion of cancer cells that express IL-17RB. Matrigel Invasion Chamber assays are useful to assess cancer cell invasiveness which reflects tumor cell ability to form invasive lesions and to metastasize (Albini A et al. (1987) "A Rapid in Vitro Assay for Quantitating the Invasive Potential of Tumor Cells" *Cancer Research* 47: 3239-3245). As shown in FIGS. 8A-8C, IL-17B increased the migration of OAW42 ovarian cancer cells (FIG. 8A) and MCF7 breast cancer cells (FIG. 8B). IL-17B increased invasiveness of OAW42 ovarian cancer cells (FIG. 8C). Interestingly, IL-17B did not increase invasion of the MDA-MB231 cells that do not express IL-17RB (FIGS. 11A-11B). Therefore, IL-17B and IL-17RB can promote cancer cell migration, invasion and metastasis.

Example 4

IL-17B and IL-17RB Promote Cancer Cell Chemoresistance

Figure 9A:
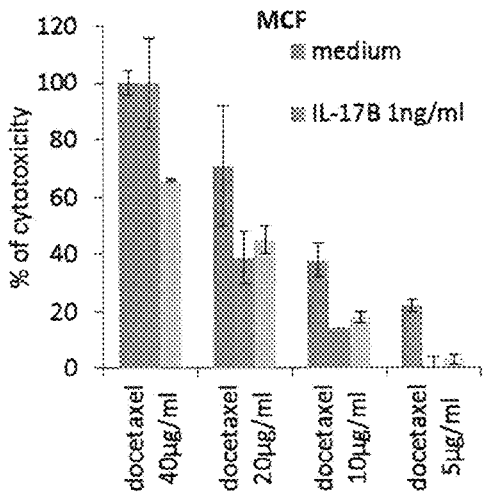
FIGS. 9A-9F: IL-17B inhibits docetaxel and doxorubicin-induced cell death. MCF7 (A), T47D (B), MDA-MB436 (C), BT20 (D) and MDA-MB468 (E) breast cells were cultured for 48 h in adequate complete medium alone (medium) or treated with recombinant human IL-17B at 1 or 10 ng/ml as indicated. Cells were then culture in Fetal Calf Serum (FCS) free medium supplemented with corresponding concentration of cytokine for 24 h and then further supplemented with docetaxel at 5, 10, 20 or 40 µg/ml as indicated for 7 h. The percentage of cell death (=cytotoxicity) was determined using the Cytotoxicity Detection Kit (Roche). (F) MCF7 cells were cultured for 48 h in adequate complete medium alone (medium) or treated with recombinant human IL-17B at 1 or 10 ng/ml as indicated. Cells were then culture in FCS free medium supplemented with corresponding concentration of cytokine for 24 h and then further supplemented with doxorubicin at 20 or 30 µM as indicated for 7 h. The percentage of cell death (=cytotoxicity) was determined using the Cytotoxicity Detection Kit (Roche).
Figure 9B:
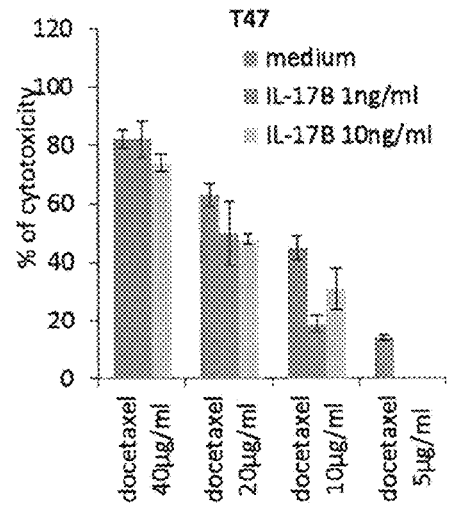
Figure 9C:
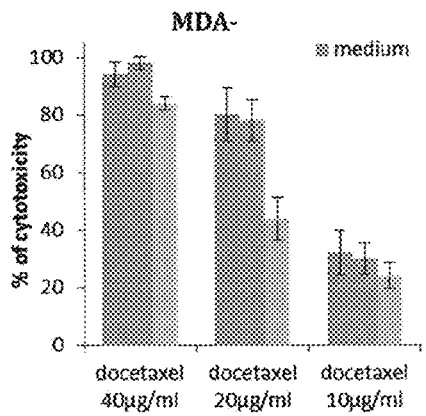
Figure 9D:
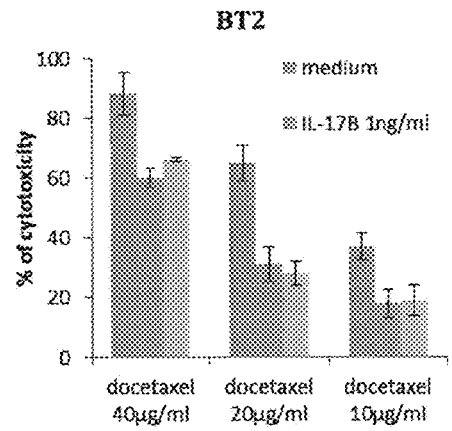
Figure 9E:
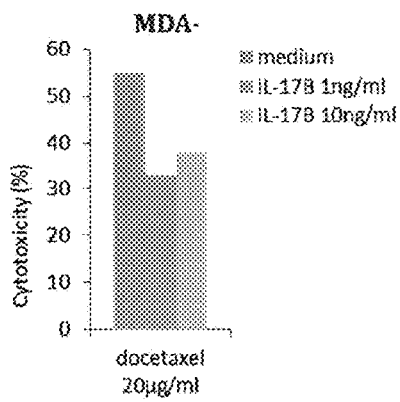
Figure 9F:
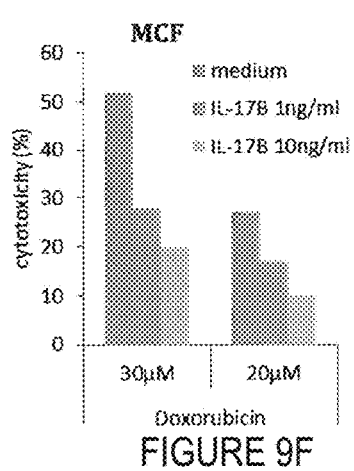

We tested whether IL-17B may promote resistance to chemotherapeutic agents such as docetaxel and doxorubicin. As illustrated in FIGS. 9A-9F, IL-17B decreased doxetaxel-induced cell death in several breast cancer cell lines that express IL-17RB (FIGS. 9A-E). Furthermore, IL-17B also protected MCF7 breast cancer cells from doxorubicin-induced cell death (FIG. 9F). Therefore, IL-17B and IL-17RB can promote chemoresistance.

Example 5

IL-17C, IL-17D and IL-17RE Stimulate Cancer Cell Proliferation

Figure 10A:
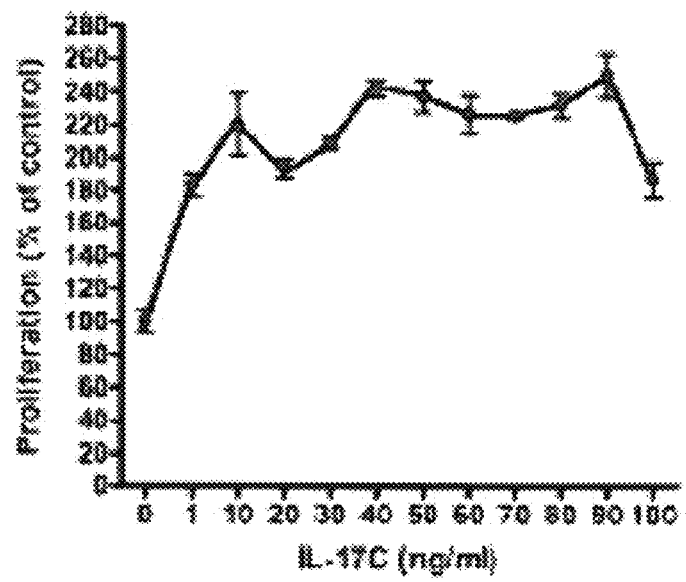
FIGS. 10A-10F: IL-17C and IL-17D increase the proliferation of breast and ovarian cancer cells. OAW42 (ovarian, A), MCF7 (breast, B) and T47D (breast, C) cells were cultured in adequate complete medium supplemented with increasing doses of recombinant human IL-17C as indicated. Cell proliferation was assessed at 72 h using tritiated thymidine ([3H]-TdR) incorporation protocol. OAW42 (D), MCF7 (E) and T47D (F) cells were cultured in adequate complete medium supplemented with increasing doses of recombinant human IL-17D as indicated. Cell proliferation was assessed at 72 h using tritiated thymidine ([3H]-TdR) incorporation protocol.
Figure 10B:
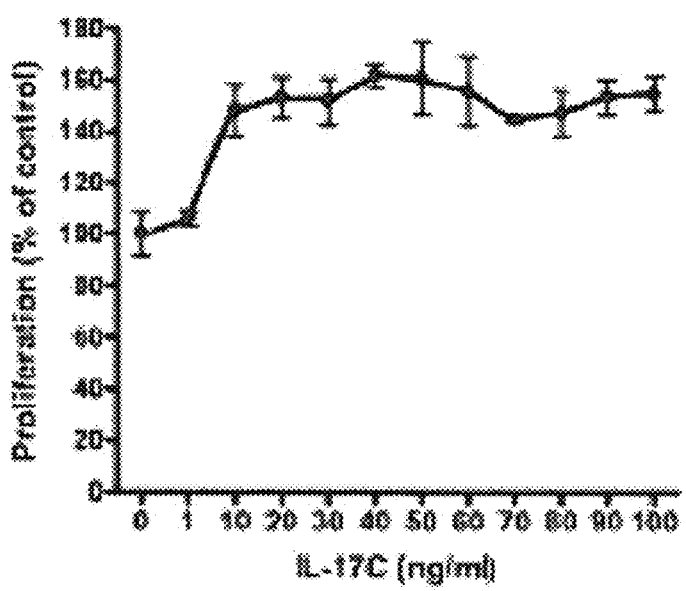
Figure 10C:
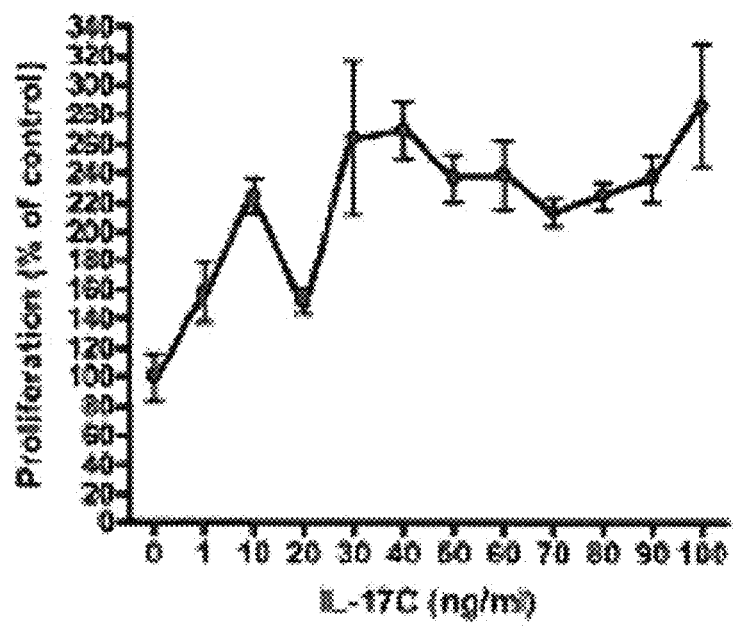
Figure 10D:
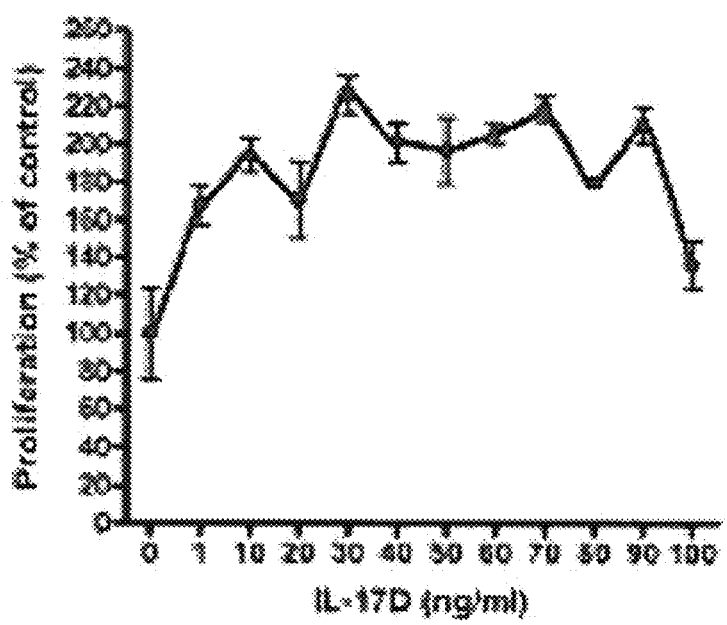
Figure 10E:
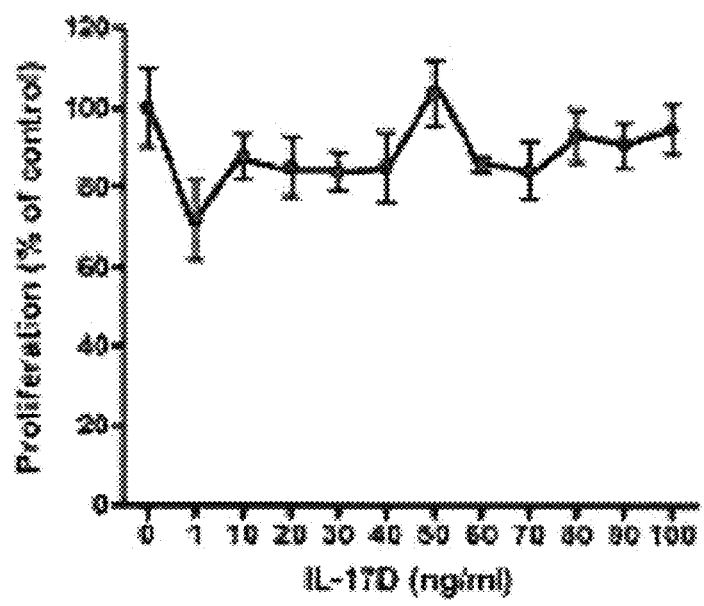
Figure 10F:
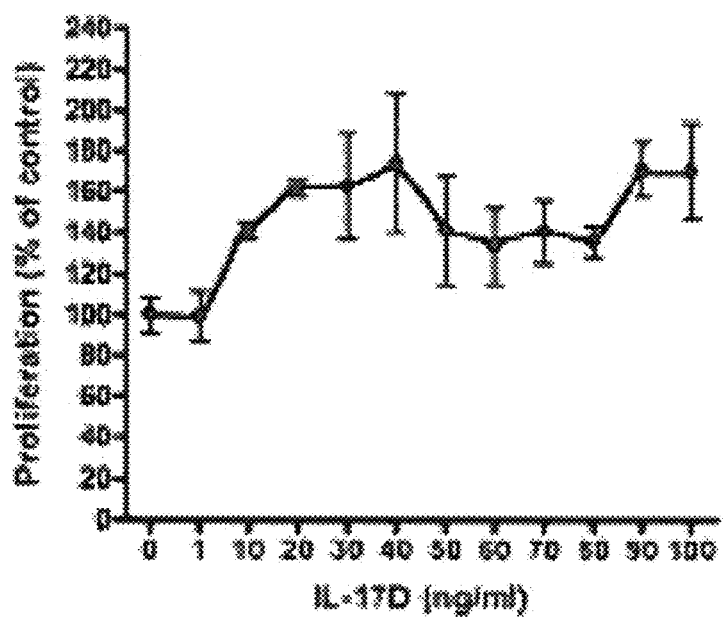

As IL-17C, IL-17D and IL-17RE are upregulated in human cancers (Example 1), we tested whether they may have oncogenic properties. We first tested whether IL-17C would alter the proliferation of human cancer cells that express IL-17RE. As shown in FIGS. 10A-C, IL-17C increased OAW42, T47D and MCF7 cancer cell proliferation. We then tested whether IL-17D would alter the proliferation of human cancer cells. As shown in FIGS. 10D-F, IL-17D increased OAW42 and MCF7 cancer cell proliferation.

Therefore, IL-17B, IL-17C and IL-17RE can promote tumor growth by increasing cancer cell proliferation.

Example 6

IL-17C, IL-17D and IL-17RE Increase Cancer Cell Invasion

We tested whether IL-17C may increase invasion of cancer cells that expressed IL-17RE. Matrigel Invasion Chamber assays are useful to assess cancer cell invasiveness which reflects tumor cell ability to form invasive lesions and to metastasize (Albini A et al. (1987) "A Rapid in Vitro Assay for Quantitating the Invasive Potential of Tumor cells "*Cancer Research* 47: 3239-3245). As shown in FIGS. 11A-11B, IL-17C increased invasiveness of MDA-MB231 breast cancer cells. We then tested whether IL-17D may increase invasion of breast cancer cells. As shown in FIGS. 11A-11B, IL-17D increased invasiveness of MDA-MB231 breast cancer cells. Therefore, IL-17C, IL-17and IL-17RE can promote cancer cell invasion and metastasis.

Example 7

Figure 12:
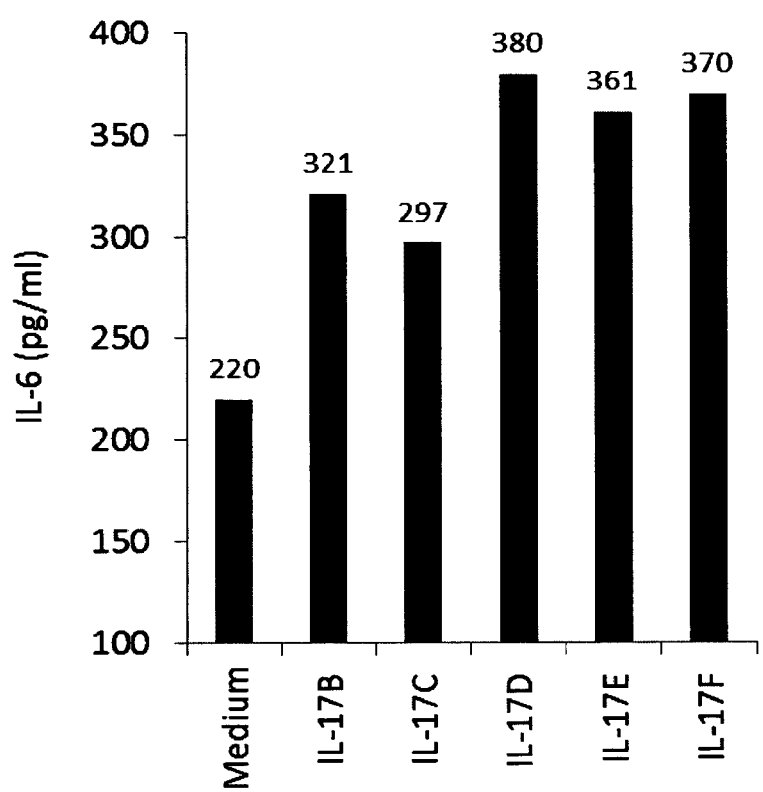
FIG. 12: IL-17B, IL-17C, IL-17D, IL-17E and IL-17F increase the production of pro-inflammatory IL-6 by normal human dermal fibroblasts (NHDF). NHDF were cultured for 24 h in complete adequate complete medium alone (medium) or in the presence of 30 ng/ml of recombinant human IL-17B, IL-17C, IL-17D, IL-17E or IL-17F as indicated. All isoforms increased the production of pro-inflammatory IL-6 by NHDF.

IL-17 Isoforms Induce the Secretion of Pro-Inflammatory IL-6 in Dermal Fibroblasts IL-17A is a known pro-inflammatory cytokine that can induce the production of various pro-inflammatory mediators such as IL-6. We therefore tested whether the other IL-17 isoforms also induce the secretion of pro-inflammatory mediators such as IL-6 by normal human dermal fibroblasts (NHDF) that express IL-17RB and IL-17RE. NHDF were stimulated with recombinant human IL-17B, IL17C or IL17D. As shown in FIG. 12, all the isoforms tested increased the secretion of IL-6 by NHDF. Therefore, IL-17B, IL17C, IL17D, IL-17RB and IL-17RE exhibit pro-inflammatory activity, and may thus be involved in chronic inflammatory diseases or auto-immune diseases.

The invention claimed is:

1. A method for treating cancer in a patient comprising the step of administering to the patient a composition comprising at least one interleukin 17 (IL-17) antagonist of one human IL-17 isoform, wherein the one human IL-17 isoform is IL-17B, wherein the IL-17 antagonist is an antibody or an antigen-binding antibody fragment, and wherein the cancer is soft tissue sarcoma, colon cancer, gastric cancer, glioma, hepatocellular carcinoma, kidney cancer, leukemia, lung cancer, lymphoma, melanoma, multiple myeloma, ovarian cancer, pancreatic cancer, prostate cancer, head and neck cancer, or thyroid cancer.

2. The method of claim 1, wherein the administering step thereby:

targets and/or kills cancer cells or cells at increased risk for becoming cancerous; and/or treats tumor metastasis.

3. The method of claim 1, wherein the composition further comprises one IL-17 antagonist of another human IL-17 isoform.

4. The method of claim 3, wherein the one IL-17 antagonist of another human IL-17 isoform is an IL-17 antagonist of human IL-17A isoform.

5. The method of claim 1, further comprising the step of administering a therapeutic agent, wherein the composition increases the effectiveness of the therapeutic agent.

6. The method of claim 5, wherein the therapeutic agent is a chemotherapeutic agent.

* * * * *